United States Patent
Sullivan

(10) Patent No.: US 9,107,653 B2
(45) Date of Patent: Aug. 18, 2015

(54) TENSIONABLE KNOTLESS ANCHORS WITH SPLICE AND METHODS OF TISSUE REPAIR

(75) Inventor: Derek Sullivan, Naples, FL (US)

(73) Assignee: Arthrex, Inc., Naples, FL (US)

( * ) Notice: Subject to any disclaimer, the term of this patent is extended or adjusted under 35 U.S.C. 154(b) by 239 days.

(21) Appl. No.: 13/615,986

(22) Filed: Sep. 14, 2012

(65) Prior Publication Data

US 2013/0096611 A1    Apr. 18, 2013

Related U.S. Application Data

(60) Provisional application No. 61/537,811, filed on Sep. 22, 2011, provisional application No. 61/663,024, filed on Jun. 22, 2012.

(51) Int. Cl.
*A61B 17/04* (2006.01)
*A61F 2/08* (2006.01)
*A61B 17/06* (2006.01)

(52) U.S. Cl.
CPC .......... *A61B 17/0401* (2013.01); *A61B 17/0466* (2013.01); *A61B 17/0485* (2013.01); *A61B 17/0487* (2013.01); *A61F 2/0811* (2013.01); *A61B 17/06166* (2013.01); *A61B 2017/0414* (2013.01); *A61B 2017/0445* (2013.01); *A61B 2017/0446* (2013.01); *A61B 2017/0458* (2013.01); *A61B 2017/0475* (2013.01); *A61B 2017/0496* (2013.01); *A61B 2017/06185* (2013.01); *A61F 2002/0852* (2013.01); *A61F 2002/0888* (2013.01)

(58) Field of Classification Search
CPC .............. A61B 17/04; A61B 17/0401; A61B 17/0466; A61B 17/0487; A61B 17/0485; A61B 2017/06185; A61B 2017/0445; A61B 2017/0475; A61B 2017/0414; A61B 17/06166; A61B 2017/0458; A61B 2017/0496; A61B 2017/0446; A61F 2/0811; A61F 2002/0888; A61F 2002/0852; F16G 11/00
USPC .......... 606/148, 232, 300, 113, 103, 304, 213
See application file for complete search history.

(56) References Cited

U.S. PATENT DOCUMENTS

| | | | |
|---|---|---|---|
| 330,087 A * | 11/1885 | Binns | 474/253 |
| 2,698,986 A * | 1/1955 | Brown | 289/1.2 |
| 3,176,316 A | 4/1965 | Bodell | |
| 4,099,750 A * | 7/1978 | McGrew | 289/1.5 |
| 4,187,558 A | 2/1980 | Dahlen et al. | |
| 4,301,551 A | 11/1981 | Dore et al. | |
| 4,400,833 A | 8/1983 | Kurland | |
| 4,776,851 A | 10/1988 | Bruchman et al. | |

(Continued)

FOREIGN PATENT DOCUMENTS

DE    299 10 202 U1    9/1999
DE    201 01 791 U1    6/2001

(Continued)

*Primary Examiner* — Amy R Weisberg
(74) *Attorney, Agent, or Firm* — Dickstein Shapiro LLP

(57) ABSTRACT

Systems and methods for soft tissue to bone repairs, without knot tying. The soft tissue repair systems include self-cinching constructs with a fixation device, a flexible strand and a shuttle/pull device attached to the flexible strand and provided within the body of the fixation device. A splice is formed by pulling on the shuttle/pull device subsequent to the fixation device being secured into the bone, to allow desired tensioning of soft tissue to be fixated or repaired relative to the bone.

17 Claims, 22 Drawing Sheets

(56) References Cited

U.S. PATENT DOCUMENTS

| | | | |
|---|---|---|---|
| 4,790,850 A | 12/1988 | Dunn et al. | |
| 4,792,336 A | 12/1988 | Hlavacek et al. | |
| 4,851,005 A | 7/1989 | Hunt et al. | |
| 4,863,471 A | 9/1989 | Mansat | |
| 4,917,700 A | 4/1990 | Aikins | |
| 4,932,972 A | 6/1990 | Dunn et al. | |
| 5,024,669 A | 6/1991 | Peterson et al. | |
| 5,026,398 A | 6/1991 | May et al. | |
| 5,062,344 A * | 11/1991 | Gerker | 87/8 |
| 5,129,902 A | 7/1992 | Goble et al. | |
| 5,156,616 A | 10/1992 | Meadows et al. | |
| 5,171,274 A | 12/1992 | Fluckiger et al. | |
| 5,211,647 A | 5/1993 | Schmieding | |
| 5,217,495 A | 6/1993 | Kaplan et al. | |
| 5,250,053 A * | 10/1993 | Snyder | 606/145 |
| 5,263,984 A | 11/1993 | Li et al. | |
| 5,266,075 A | 11/1993 | Clark et al. | |
| 5,306,301 A | 4/1994 | Graf et al. | |
| 5,320,626 A | 6/1994 | Schmieding | |
| 5,397,357 A | 3/1995 | Schmieding et al. | |
| 5,534,011 A * | 7/1996 | Greene et al. | 606/232 |
| 5,562,669 A | 10/1996 | McGuire | |
| 5,575,819 A | 11/1996 | Amis | |
| 5,628,756 A | 5/1997 | Barker et al. | |
| 5,643,266 A | 7/1997 | Li | |
| 5,645,588 A | 7/1997 | Graf et al. | |
| 5,690,676 A * | 11/1997 | DiPoto et al. | 606/232 |
| 5,699,657 A * | 12/1997 | Paulson | 57/22 |
| 5,931,869 A | 8/1999 | Boucher et al. | |
| 5,961,520 A | 10/1999 | Beck et al. | |
| 5,964,764 A | 10/1999 | West, Jr. et al. | |
| 6,056,752 A | 5/2000 | Roger | |
| 6,099,530 A | 8/2000 | Simonian et al. | |
| 6,099,568 A | 8/2000 | Simonian et al. | |
| 6,110,207 A | 8/2000 | Eichhorn et al. | |
| 6,159,234 A | 12/2000 | Bonutti et al. | |
| 6,193,754 B1 | 2/2001 | Seedhom | |
| 6,203,572 B1 | 3/2001 | Johnson et al. | |
| 6,283,996 B1 | 9/2001 | Chervitz et al. | |
| 6,296,659 B1 | 10/2001 | Foerster | |
| 6,325,804 B1 | 12/2001 | Wenstrom et al. | |
| 6,517,542 B1 * | 2/2003 | Papay et al. | 606/232 |
| 6,517,578 B2 | 2/2003 | Hein | |
| 6,533,802 B2 | 3/2003 | Bojarski et al. | |
| 6,592,609 B1 * | 7/2003 | Bonutti | 606/232 |
| 6,991,636 B2 * | 1/2006 | Rose | 606/148 |
| 7,097,654 B1 | 8/2006 | Freedland | |
| 7,217,279 B2 * | 5/2007 | Reese | 606/232 |
| 7,261,716 B2 * | 8/2007 | Strobel et al. | 606/314 |
| 7,320,701 B2 * | 1/2008 | Haut et al. | 606/232 |
| 7,494,506 B2 | 2/2009 | Brulez et al. | |
| 7,686,838 B2 | 3/2010 | Wolf et al. | |
| 7,713,286 B2 * | 5/2010 | Singhatat | 606/232 |
| 7,749,250 B2 | 7/2010 | Stone et al. | |
| 7,776,039 B2 | 8/2010 | Bernstein et al. | |
| 7,819,898 B2 | 10/2010 | Stone et al. | |
| 7,828,855 B2 | 11/2010 | Ellis et al. | |
| 7,875,052 B2 * | 1/2011 | Kawaura et al. | 606/213 |
| 7,875,057 B2 | 1/2011 | Cook et al. | |
| 7,905,903 B2 | 3/2011 | Stone et al. | |
| 7,914,539 B2 | 3/2011 | Stone et al. | |
| 7,938,847 B2 * | 5/2011 | Fanton et al. | 606/232 |
| 8,029,536 B2 * | 10/2011 | Sorensen et al. | 606/232 |
| 8,088,130 B2 * | 1/2012 | Kaiser et al. | 606/139 |
| 8,109,965 B2 | 2/2012 | Stone et al. | |
| 8,118,836 B2 | 2/2012 | Denham et al. | |
| 8,162,997 B2 | 4/2012 | Struhl | |
| 8,206,446 B1 | 6/2012 | Montgomery | |
| 8,231,654 B2 | 7/2012 | Kaiser et al. | |
| 8,277,484 B2 * | 10/2012 | Barbieri et al. | 606/232 |
| 8,460,322 B2 * | 6/2013 | van der Burg et al. | 606/144 |
| 8,460,340 B2 * | 6/2013 | Sojka et al. | 606/232 |
| 8,652,171 B2 * | 2/2014 | Stone et al. | 606/232 |
| 8,652,172 B2 * | 2/2014 | Denham et al. | 606/232 |
| 8,758,406 B2 * | 6/2014 | Fanton et al. | 606/232 |
| 8,771,315 B2 * | 7/2014 | Lunn et al. | 606/232 |
| 8,814,905 B2 * | 8/2014 | Sengun et al. | 606/232 |
| 8,821,543 B2 * | 9/2014 | Hernandez et al. | 606/232 |
| 8,821,545 B2 * | 9/2014 | Sengun | 606/232 |
| 8,932,331 B2 * | 1/2015 | Kaiser et al. | 606/232 |
| 8,936,621 B2 * | 1/2015 | Denham et al. | 606/232 |
| 2001/0041938 A1 | 11/2001 | Hein | |
| 2002/0052629 A1 * | 5/2002 | Morgan et al. | 606/232 |
| 2002/0161439 A1 | 10/2002 | Strobel et al. | |
| 2003/0114929 A1 | 6/2003 | Knudsen et al. | |
| 2004/0015171 A1 | 1/2004 | Bojarski et al. | |
| 2004/0059415 A1 | 3/2004 | Schmieding | |
| 2004/0073306 A1 | 4/2004 | Eichhorn et al. | |
| 2004/0243235 A1 | 12/2004 | Goh et al. | |
| 2004/0267360 A1 | 12/2004 | Huber | |
| 2005/0004670 A1 | 1/2005 | Gebhardt et al. | |
| 2005/0033363 A1 | 2/2005 | Bojarski et al. | |
| 2005/0065533 A1 | 3/2005 | Magen et al. | |
| 2005/0070906 A1 | 3/2005 | Clark et al. | |
| 2005/0137704 A1 | 6/2005 | Steenlage | |
| 2005/0149187 A1 | 7/2005 | Clark et al. | |
| 2005/0171603 A1 | 8/2005 | Justin et al. | |
| 2005/0203623 A1 | 9/2005 | Steiner et al. | |
| 2005/0261766 A1 | 11/2005 | Chervitz et al. | |
| 2006/0067971 A1 | 3/2006 | Story et al. | |
| 2006/0095130 A1 | 5/2006 | Caborn et al. | |
| 2006/0142769 A1 | 6/2006 | Collette | |
| 2006/0265064 A1 | 11/2006 | Re et al. | |
| 2007/0021839 A1 | 1/2007 | Lowe | |
| 2007/0083236 A1 | 4/2007 | Sikora et al. | |
| 2007/0118217 A1 | 5/2007 | Brulez et al. | |
| 2007/0156148 A1 * | 7/2007 | Fanton et al. | 606/72 |
| 2007/0162123 A1 | 7/2007 | Whittaker et al. | |
| 2007/0162125 A1 | 7/2007 | LeBeau et al. | |
| 2007/0179531 A1 | 8/2007 | Thornes | |
| 2007/0185494 A1 * | 8/2007 | Reese | 606/72 |
| 2007/0203508 A1 | 8/2007 | White et al. | |
| 2007/0225805 A1 | 9/2007 | Schmieding | |
| 2007/0239209 A1 | 10/2007 | Fallman | |
| 2007/0239275 A1 | 10/2007 | Willobee | |
| 2007/0250163 A1 | 10/2007 | Cassani | |
| 2007/0270857 A1 | 11/2007 | Lombardo et al. | |
| 2008/0009904 A1 * | 1/2008 | Bourque et al. | 606/232 |
| 2008/0046009 A1 | 2/2008 | Albertorio et al. | |
| 2008/0109037 A1 * | 5/2008 | Steiner et al. | 606/232 |
| 2008/0140092 A1 * | 6/2008 | Stone et al. | 606/144 |
| 2008/0177302 A1 | 7/2008 | Shurnas | |
| 2008/0188935 A1 | 8/2008 | Saylor et al. | |
| 2008/0188936 A1 | 8/2008 | Ball et al. | |
| 2008/0208252 A1 | 8/2008 | Holmes | |
| 2008/0215150 A1 | 9/2008 | Koob et al. | |
| 2008/0228271 A1 | 9/2008 | Stone et al. | |
| 2008/0234819 A1 | 9/2008 | Schmieding et al. | |
| 2008/0243248 A1 | 10/2008 | Stone et al. | |
| 2008/0255613 A1 * | 10/2008 | Kaiser et al. | 606/232 |
| 2008/0275553 A1 | 11/2008 | Wolf et al. | |
| 2008/0275554 A1 | 11/2008 | Iannarone et al. | |
| 2008/0300683 A1 | 12/2008 | Altman et al. | |
| 2008/0312689 A1 | 12/2008 | Denham et al. | |
| 2009/0018654 A1 | 1/2009 | Schmieding et al. | |
| 2009/0030516 A1 | 1/2009 | Imbert | |
| 2009/0054982 A1 | 2/2009 | Cimino | |
| 2009/0062854 A1 | 3/2009 | Kaiser et al. | |
| 2009/0069847 A1 * | 3/2009 | Hashiba et al. | 606/232 |
| 2009/0082805 A1 | 3/2009 | Kaiser et al. | |
| 2009/0187244 A1 | 7/2009 | Dross | |
| 2009/0192546 A1 * | 7/2009 | Schmieding et al. | 606/232 |
| 2009/0216326 A1 | 8/2009 | Hirpara et al. | |
| 2009/0228017 A1 | 9/2009 | Collins | |
| 2009/0234451 A1 | 9/2009 | Manderson | |
| 2009/0265003 A1 | 10/2009 | Re et al. | |
| 2009/0275950 A1 | 11/2009 | Sterrett et al. | |
| 2009/0306776 A1 | 12/2009 | Murray | |
| 2009/0306784 A1 | 12/2009 | Blum | |
| 2009/0312776 A1 * | 12/2009 | Kaiser et al. | 606/148 |
| 2010/0049258 A1 | 2/2010 | Dougherty | |
| 2010/0049319 A1 | 2/2010 | Dougherty | |
| 2010/0100182 A1 | 4/2010 | Barnes et al. | |
| 2010/0145384 A1 | 6/2010 | Stone et al. | |

(56) References Cited

U.S. PATENT DOCUMENTS

| | | |
|---|---|---|
| 2010/0145448 A1 | 6/2010 | Montes De Oca Balderas et al. |
| 2010/0211075 A1 | 8/2010 | Stone |
| 2010/0211173 A1 | 8/2010 | Bardos et al. |
| 2010/0249930 A1 | 9/2010 | Myers |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292733 A1* | 11/2010 | Hendricksen et al. ........ 606/232 |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0071545 A1 | 3/2011 | Pamichev et al. |
| 2011/0087283 A1* | 4/2011 | Donnelly et al. ............ 606/232 |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0218625 A1 | 9/2011 | Berelsman et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053627 A1* | 3/2012 | Sojka et al. .................. 606/232 |
| 2012/0053630 A1* | 3/2012 | Denham et al. ............. 606/232 |
| 2012/0065732 A1 | 3/2012 | Roller et al. |
| 2012/0089143 A1 | 4/2012 | Martin et al. |
| 2012/0089193 A1* | 4/2012 | Stone et al. ................... 606/301 |
| 2012/0109299 A1 | 5/2012 | Li et al. |
| 2012/0123473 A1* | 5/2012 | Hernandez ................... 606/232 |
| 2012/0123474 A1 | 5/2012 | Zajac et al. |
| 2012/0123541 A1* | 5/2012 | Albertorio et al. ......... 623/13.14 |
| 2012/0130424 A1* | 5/2012 | Sengun et al. ............... 606/232 |
| 2012/0150297 A1 | 6/2012 | Denham et al. |
| 2012/0158051 A1* | 6/2012 | Foerster ........................ 606/232 |
| 2012/0165867 A1* | 6/2012 | Denham et al. ............. 606/232 |
| 2012/0165938 A1 | 6/2012 | Denham et al. |
| 2012/0179199 A1* | 7/2012 | Hernandez et al. .......... 606/232 |
| 2012/0197271 A1 | 8/2012 | Astorino et al. |
| 2012/0239085 A1* | 9/2012 | Schlotterback et al. ...... 606/228 |
| 2012/0290003 A1* | 11/2012 | Dreyfuss ...................... 606/232 |
| 2012/0296345 A1 | 11/2012 | Wack et al. |
| 2012/0330357 A1* | 12/2012 | Thal ............................. 606/232 |
| 2013/0023928 A1 | 1/2013 | Dreyfuss |
| 2013/0023929 A1 | 1/2013 | Sullivan et al. |
| 2013/0072975 A1* | 3/2013 | Van Der Burg et al. ...... 606/232 |
| 2013/0085528 A1* | 4/2013 | DiMatteo et al. ............ 606/232 |
| 2013/0123842 A1* | 5/2013 | Chan et al. .................... 606/232 |
| 2013/0131723 A1* | 5/2013 | Snell et al. .................... 606/232 |
| 2013/0144338 A1* | 6/2013 | Stone et al. .................. 606/232 |
| 2013/0190819 A1* | 7/2013 | Norton ......................... 606/232 |
| 2013/0345749 A1* | 12/2013 | Sullivan et al. ............... 606/232 |
| 2013/0345750 A1* | 12/2013 | Sullivan ....................... 606/232 |
| 2014/0039551 A1* | 2/2014 | Donahue ...................... 606/232 |
| 2014/0052179 A1* | 2/2014 | Dreyfuss et al. ............. 606/232 |
| 2014/0121700 A1* | 5/2014 | Dreyfuss et al. ............. 606/232 |
| 2014/0142627 A1* | 5/2014 | Hendricksen et al. ........ 606/232 |
| 2014/0257378 A1* | 9/2014 | Norton et al. ................ 606/228 |
| 2014/0257382 A1* | 9/2014 | McCartney .................. 606/232 |
| 2014/0257384 A1* | 9/2014 | Dreyfuss et al. ............. 606/232 |
| 2014/0276992 A1* | 9/2014 | Stone et al. ................... 606/148 |

FOREIGN PATENT DOCUMENTS

| | | |
|---|---|---|
| EP | 0 440 991 A1 | 8/1991 |
| EP | 1 108 401 A1 | 6/2001 |
| EP | 1 707 127 A1 | 10/2006 |
| WO | WO 03/022161 A1 | 3/2003 |
| WO | WO 2006/037131 A2 | 4/2006 |
| WO | WO 2007/002561 A1 | 1/2007 |
| WO | WO 2007/109769 A1 | 9/2007 |
| WO | WO 2008/091690 A1 | 7/2008 |

* cited by examiner

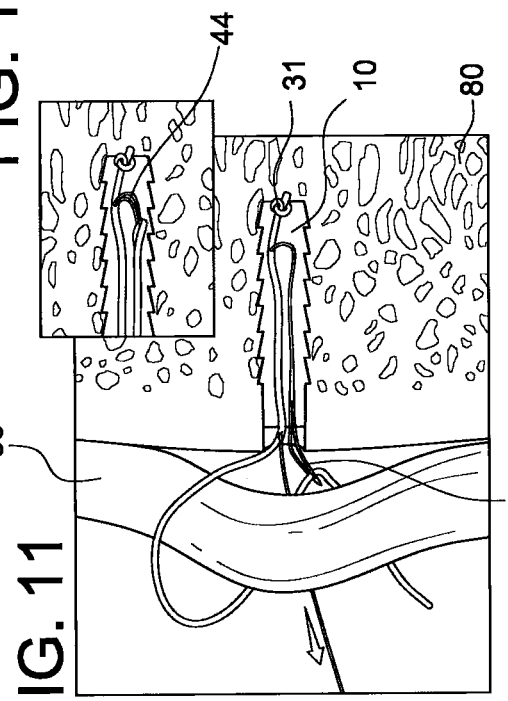
FIG. 10
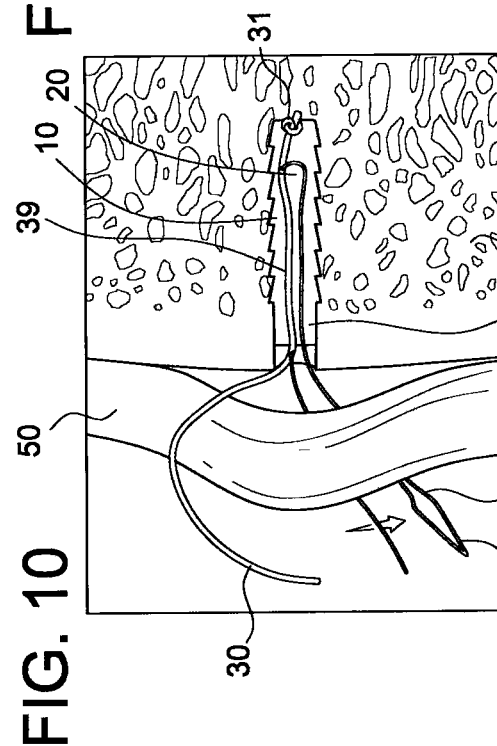
FIG. 11
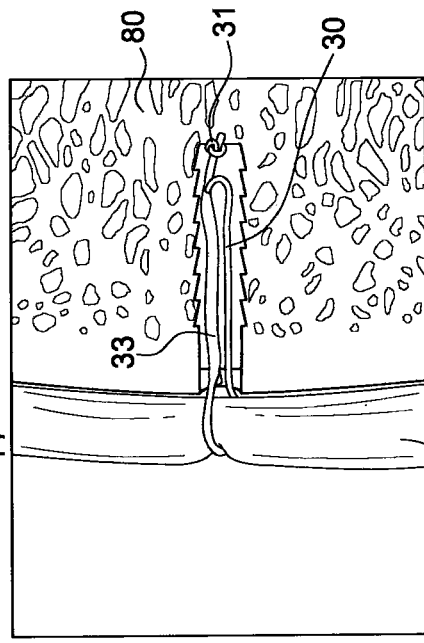
FIG. 12
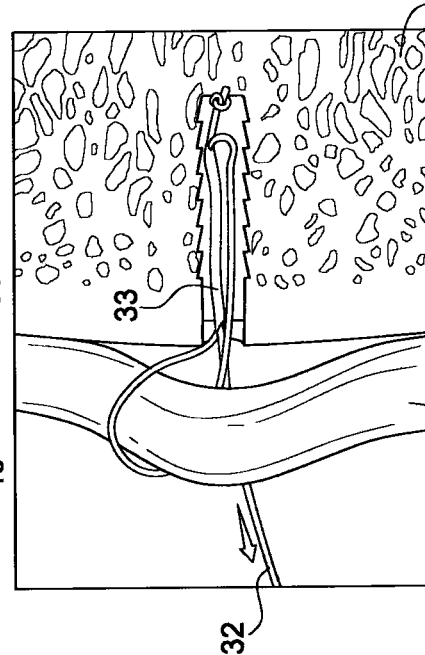
FIG. 13
FIG. 14

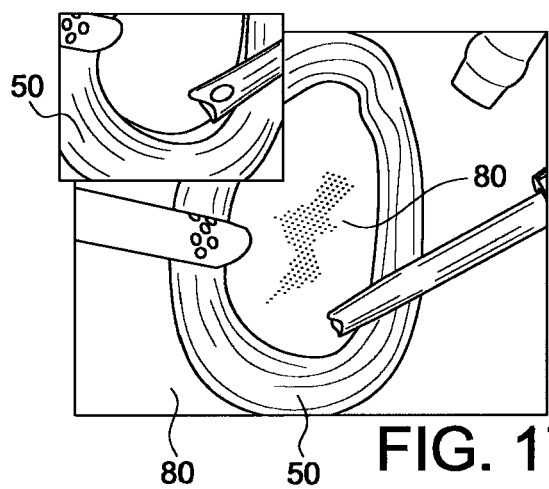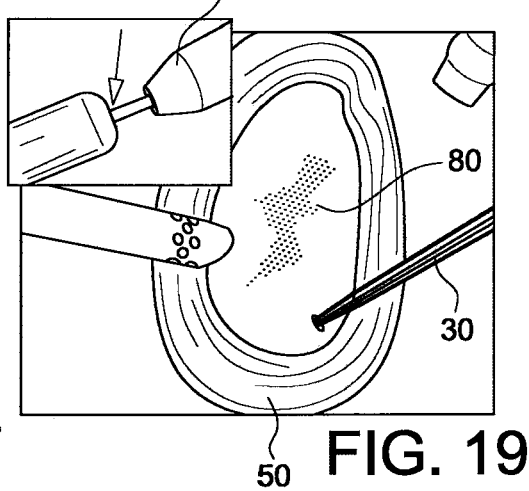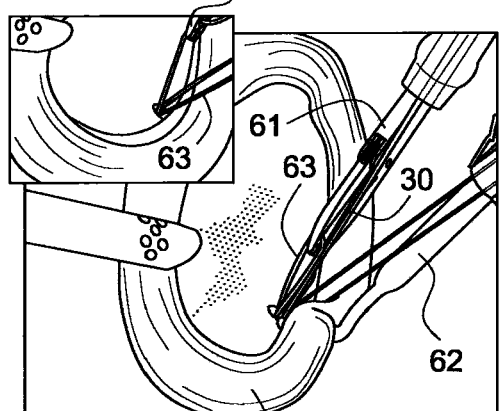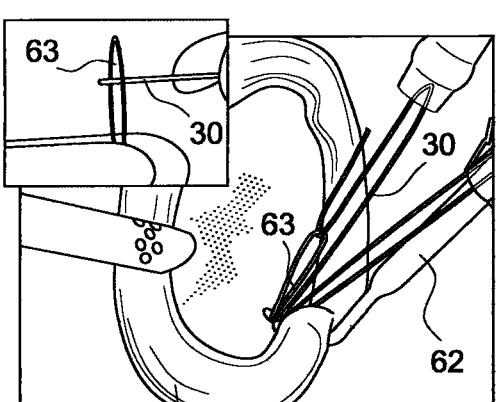

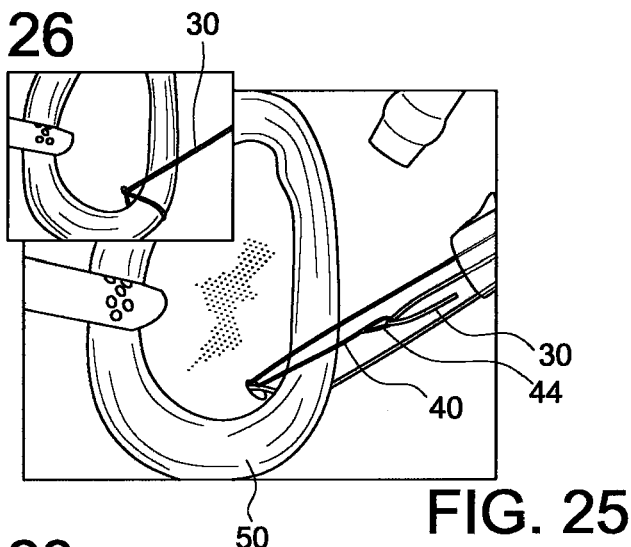
FIG. 26
FIG. 25
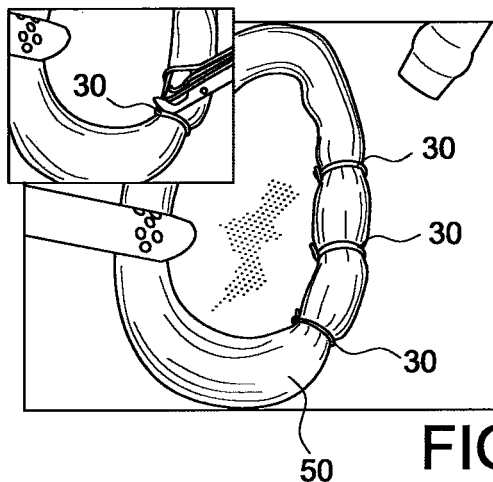
FIG. 28
FIG. 27
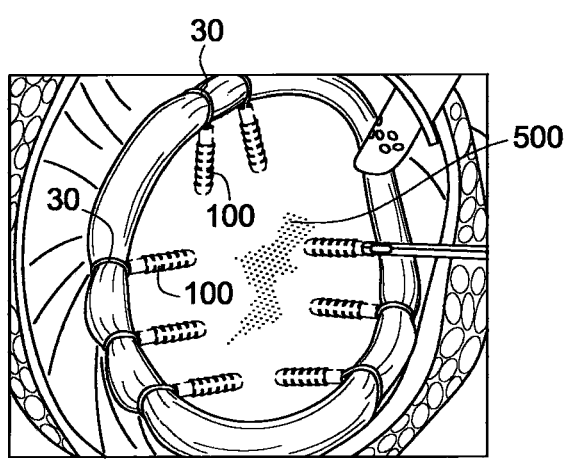
FIG. 29
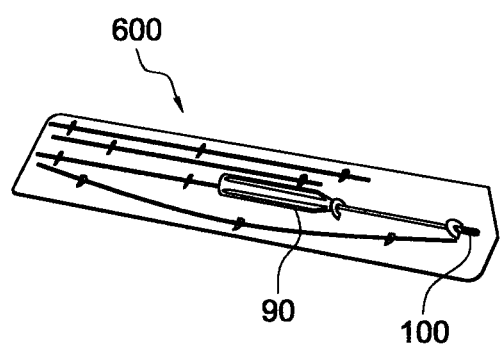
FIG. 30

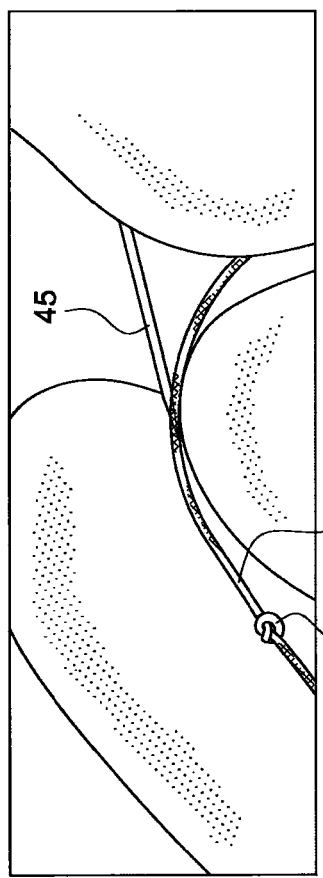
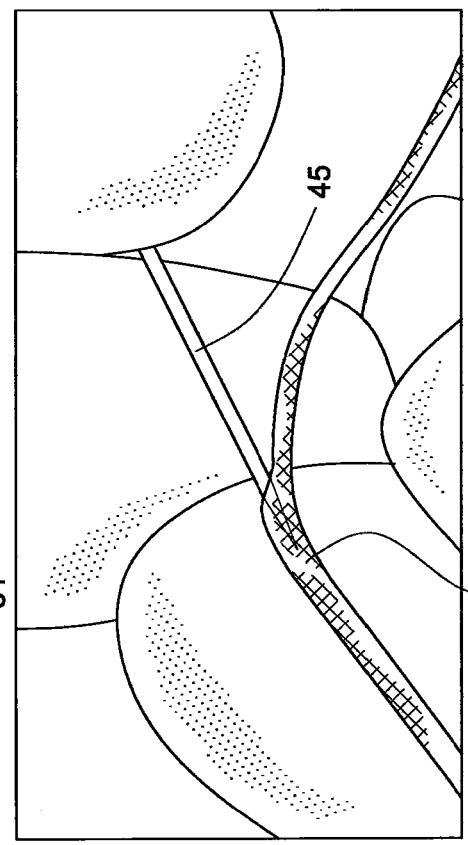
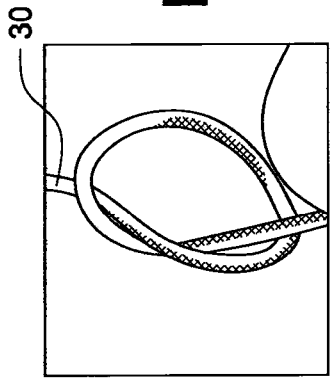
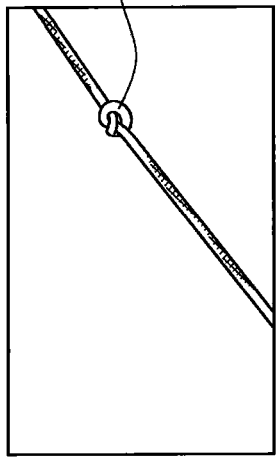
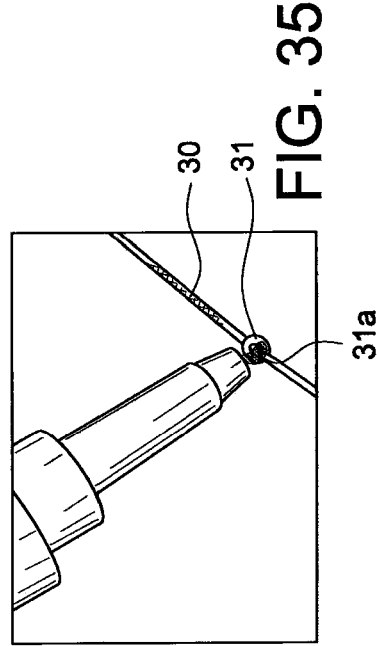

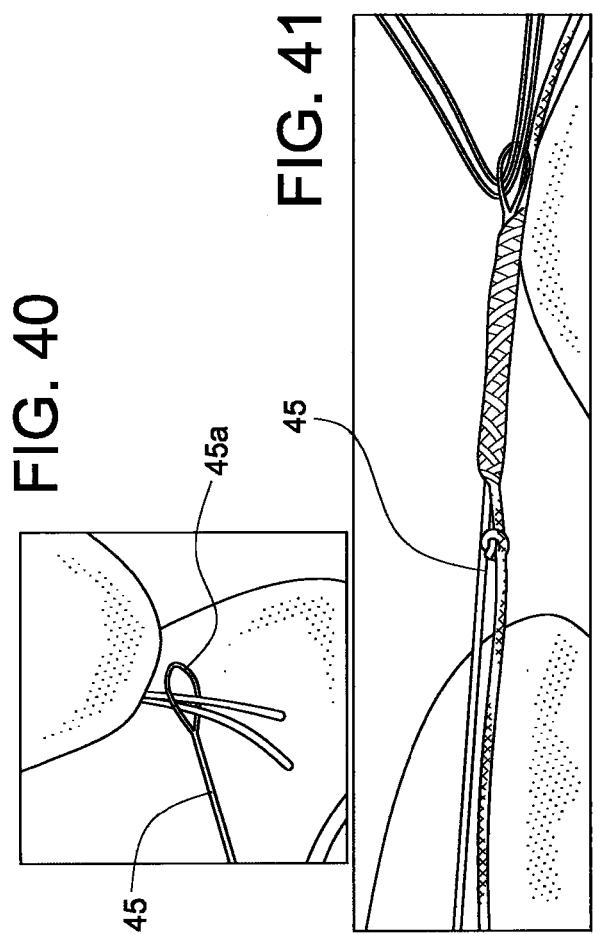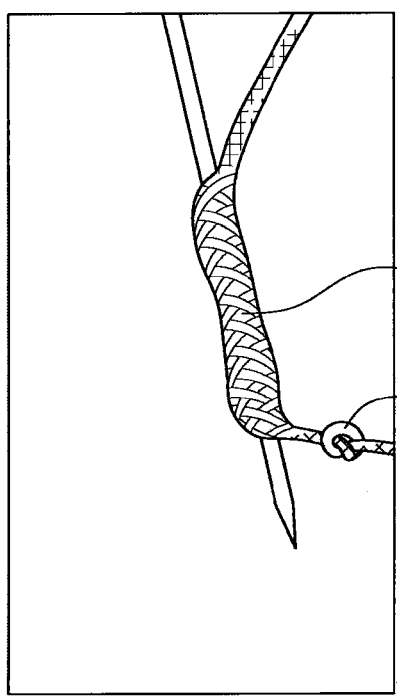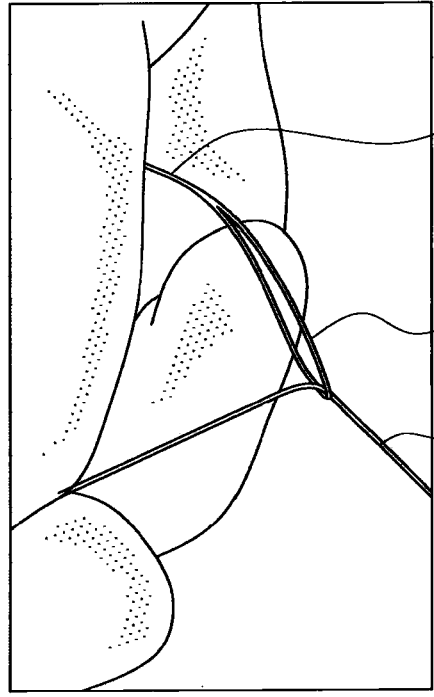

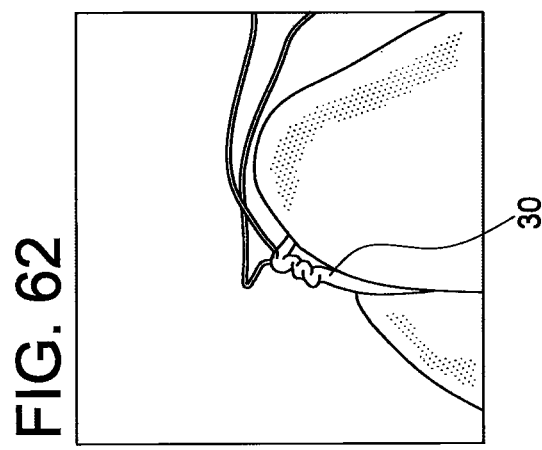
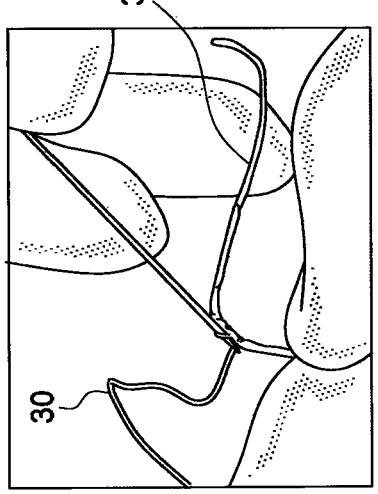
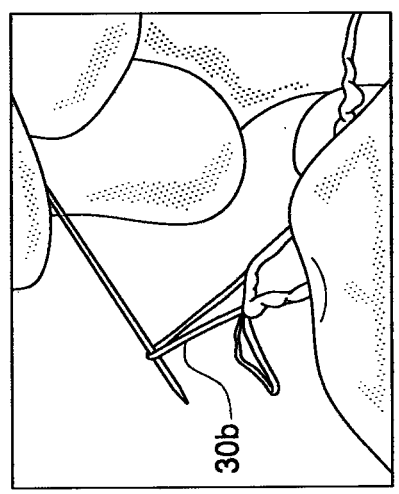
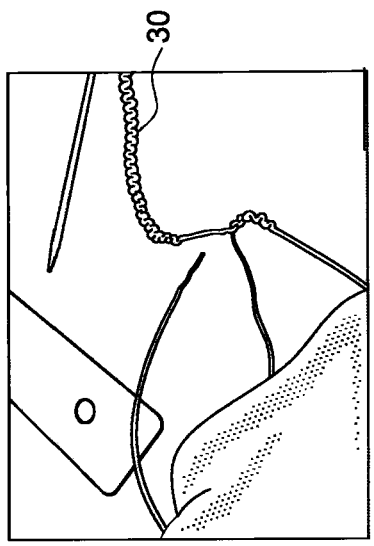
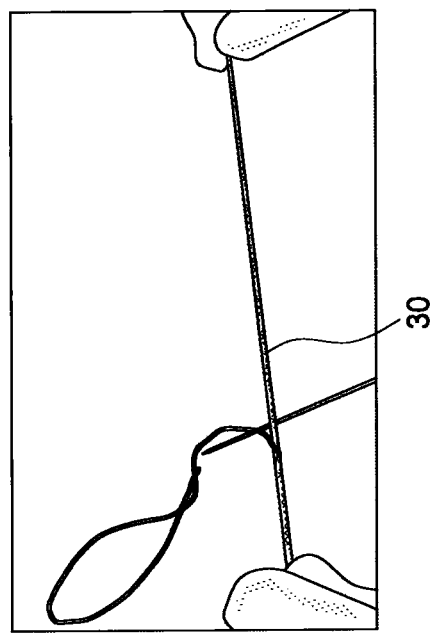

TENSIONABLE KNOTLESS ANCHORS WITH SPLICE AND METHODS OF TISSUE REPAIR

CROSS-REFERENCE TO RELATED APPLICATIONS

This application claims the benefit of U.S. Provisional Application No. 61/537,811, filed Sep. 22, 2011, and of U.S. Provisional Application No. 61/663,024, filed Jun. 22, 2012, the disclosures of both of which are incorporated by reference in their entirety herein.

FIELD OF THE INVENTION

The present invention relates to surgical devices and, in particular, to devices for repair or fixation of soft tissue to bone without the need for knots.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors, such as the two piece Arthrex PushLock® anchor, disclosed in U.S. Pat. No. 7,329,272, have been developed to facilitate tissue fixation to bone.

There is a need for a knotless anchor which has a design that allows tensioning of the suture as necessary and after insertion into bone. Also needed is a tensionable anchor that does not require tying of knots and allows adjustment of both the tension of the suture and the location of the tissue with respect to the bone.

SUMMARY OF THE INVENTION

The present invention fulfills the above needs and objectives by providing a knotless, tensionable suture anchor. The suture anchor of the present invention has a configuration which allows the suture to be spliced and passed through itself within the suture anchor, to create a construct that is tensionable after insertion in bone (to allow attached tissue to be brought proximate to bone) and does not require tying of any knots.

Other features and advantages of the present invention will become apparent from the following description of the invention.

BRIEF DESCRIPTION OF THE DRAWINGS

FIGS. 10-14 illustrate subsequent steps of a method of knotless SutureTak™ self-locking technology according to a method of the present invention (and with the surgical construct of FIGS. 2-5).

FIGS. 17-30 illustrate subsequent steps of an exemplary method of tissue repair (rotator cuff repair) with a surgical construct of the present invention.

FIGS. 31-72 illustrate subsequent steps of a method of assembling a surgical construct of the present invention (with a tensionable knotless anchor (knotless SutureTak), suture and suture passing device attached to the suture).

DETAILED DESCRIPTION OF THE EMBODIMENTS

Figure 1:
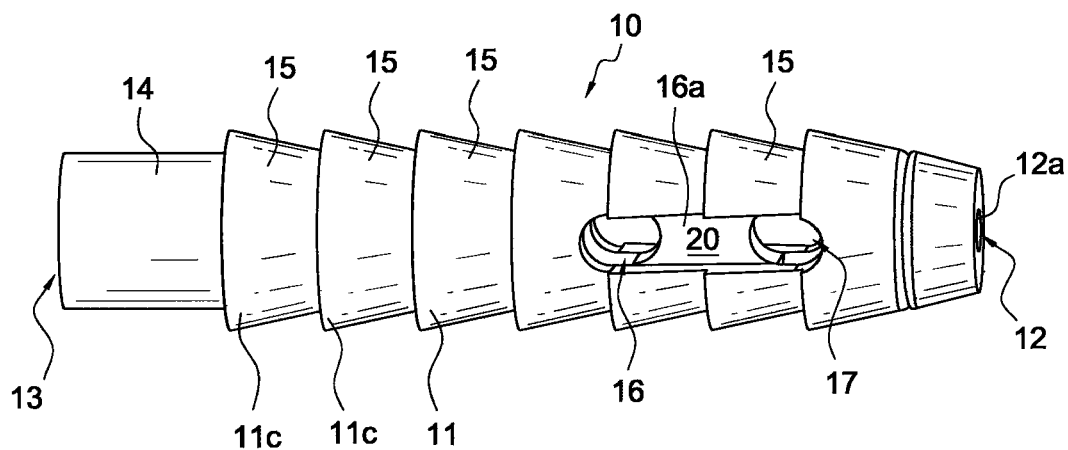
FIG. 1 illustrates a tensionable knotless anchor according to an exemplary embodiment of the present invention.

The present invention provides surgical constructs, systems and techniques for knotless soft tissue repair and fixation, such as fixation of soft tissue (ligament, tendon, graft, etc.) to bone. The surgical constructs comprise fixation devices (tensionable knotless anchors) that are inserted into bone with a suture mechanism (tensionable construct) formed of a flexible strand (a suture) provided within the fixation device and a shuttle/pull device (a suture passing instrument) attached to the flexible strand. The flexible strand and the shuttle/pull device attached to it allow the formation of a splice within or outside the body of the anchor and during the tissue repair procedure (to finalize the construct). The shuttle/pull device is provided within the strand (inside of the strand) and forms the splice subsequent to the insertion of the fixation device within the bone (and subsequent to attachment to soft tissue to be repaired or fixated) to allow formation of the final fixation device with a knotless self-locking mechanism that allows the user (for example, the surgeon) to control the tension of the strand on the soft tissue to be attached to bone.

At least one of the flexible strand and the shuttle/pull device may be made of any known suture material, such as ultrahigh molecular weight poly ethylene (UHMWPE) or the FiberWire® suture (disclosed in U.S. Pat. No. 6,716,234 which is hereby incorporated by reference in its entirety). Typically the suture will be UHWMPE suture without a core to permit ease of splicing. The shuttle/pull device may be a shuttle/pull suture device such as a FiberLink™ or a Nitinol loop.

The present invention also provides methods of soft tissue repair which do not require tying of knots and allow adjustment of both the tension of the suture and the location of the tissue with respect to the bone. An exemplary method of the present invention comprises inter alia the steps of: (i) providing a surgical construct comprising a fixation device (for example, an anchor) with a flexible strand (for example, suture) and with a shuttle/pull device (a suture passing instrument) attached to the flexible strand; (ii) inserting the fixation device into bone; (iii) passing the flexible strand around or through tissue to be fixated (or reattached) to bone, and then through an eyelet/loop of the shuttle/pull device; (iv) subsequently, pulling on the shuttle/pull device to allow the flexible strand to pass through itself and to form a splice; and (v) pulling on the flexible strand to allow the soft tissue to achieve the desired location relative to the bone, and to allow proper tensioning of the final construct.

The flexible strand may be passed through at least a portion of the body of the fixation device (for example, through a full cannulation of the fixation device, or through a transversal opening at a distal end of the fixation device). Alternatively, the flexible strand may be fixed to the fixation device (which may be solid or cannulated) by overmolding the suture to the anchor body or by compressing the suture against the bone (achieving an interference fit between the fixation device and the bone tunnel, compressing the flexible strand). The splice may be formed within the body of the fixation device or outside the body of the fixation device. Upon insertion into the bone and tensioning, the splice may reside within the body of the fixation device or outside the body of the fixation device (but within a bone tunnel).

Another exemplary method of the present invention comprises inter alia the steps of: (i) providing a surgical construct comprising a fixation device (for example, an anchor) with a flexible strand (for example, suture) extending through the body of the fixation device and with a shuttle/pull device (a suture passing instrument) attached to the flexible strand; (ii) inserting the fixation device into bone; (iii) passing the flexible strand around or through tissue to be fixated (or reattached) to bone, and then through an eyelet/loop of the shuttle/pull device; (iv) subsequently, pulling on the shuttle/pull device to allow the flexible strand to pass through itself and to form a splice within the body of the fixation device (with the flexible strand passing through itself); and (v) pulling on the flexible strand to allow the soft tissue to achieve the desired location relative to the bone, and to allow proper tensioning of the final construct.

According to another exemplary method of the present invention, a method of tissue repair comprises inter alia the steps of: (i) providing a surgical construct comprising a fixation device (for example, an anchor) with a flexible strand (for example, suture) fixed to the fixation device and with a shuttle/pull device (a suture passing instrument) attached to the flexible strand; (ii) inserting the fixation device into bone; (iii) passing the flexible strand around or through tissue to be fixated (or reattached) to bone, and then through an eyelet/loop of the shuttle/pull device; (iv) subsequently, pulling on the shuttle/pull device to allow the flexible strand to pass through itself and to form a splice outside the body of the fixation device (i.e., with the flexible strand passing through itself and the splice being located outside the body of the fixation device); and (v) pulling on the flexible strand to allow the soft tissue to achieve the desired location relative to the bone, and to allow proper tensioning of the final construct.

Figure 3:
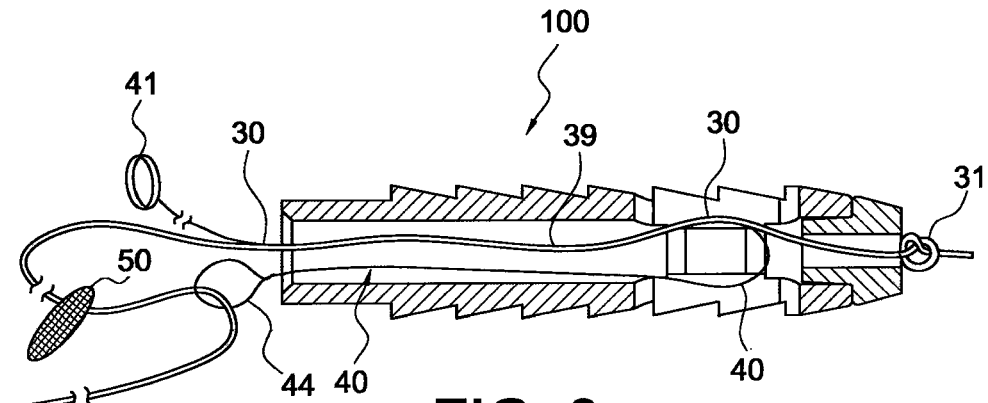
FIG. 3 illustrates the surgical construct of FIG. 2 with the suture threaded through the suture passing device.
Figure 4:
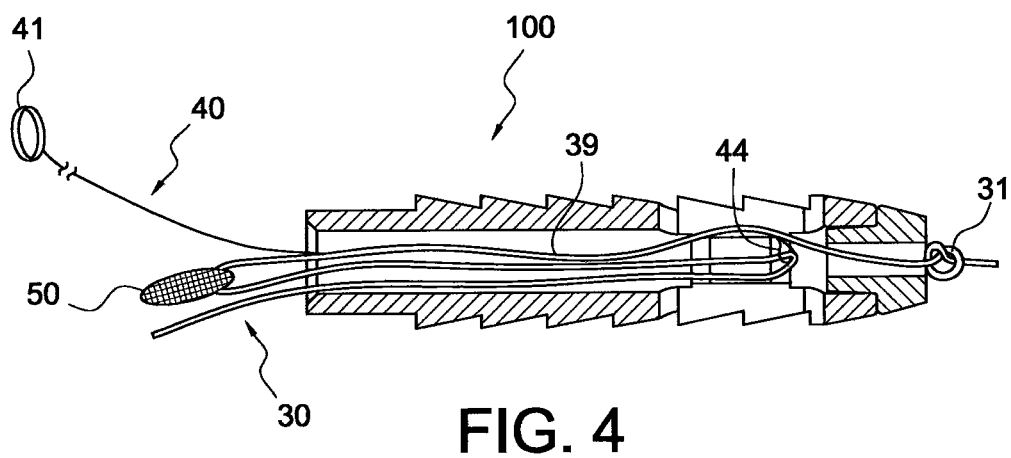
FIG. 4 illustrates the surgical construct of FIG. 3 during tensioning, wherein the suture has been pulled so that the suture passes through itself.
Figure 5:
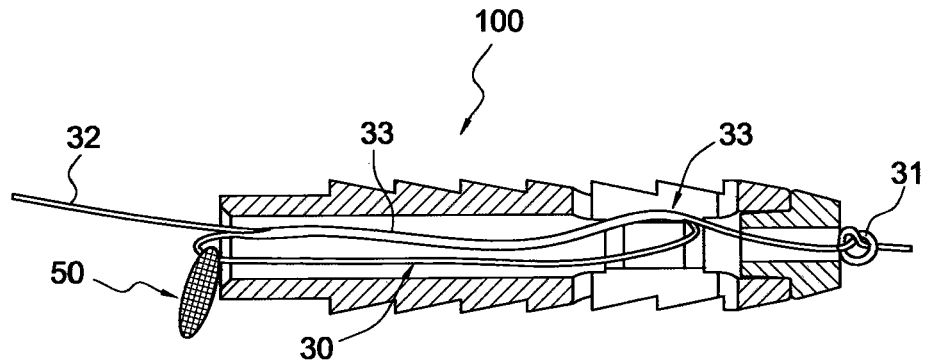
FIG. 5 illustrates the surgical construct of FIG. 4 after tensioning, wherein the suture has been pulled through itself to create a splice and the tissue has been pulled towards the bone.
Figure 8:
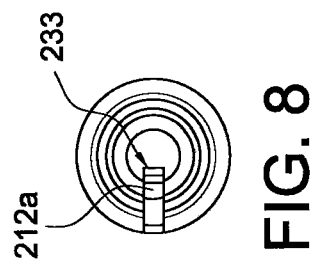
FIG. 8 is a right side view of the tensionable knotless anchor of FIG. 6.

Referring now to the drawings, where like elements are designated by like reference numerals, FIGS. 1-5 illustrate an exemplary fixation device 10 of the present invention employed to assemble surgical construct 100 (FIG. 5). In the particular exemplary embodiment illustrated in FIG. 1, fixation device 10 is a tensionable knotless anchor having an anchor body 11 provided with a longitudinal axis 11*a*, a proximal end 13 and a distal end 12, and a plurality of ribs 15 extending circumferentially around it. Openings/channels 16 and 17 allow threading suture(s) and/or suture passing device(s) to pass around post 20, as detailed below. Cannulation 11*b* extends along the body 11 to allow passage of flexible strands and of suture passing devices, as detailed below.

Cylindrical portion 14 is provided at the proximal end 13 of the anchor 10 and contains a socket 19 (FIG. 2) configured to securely engage a tip of a driver.

Openings/channels 16, 17 are positioned opposite to each other relative to the post 20 and also symmetrically located relative to the post 20, to allow flexible strand 30 (suture 30) and shuttle/pull device 40 (suture passing instrument 40) to pass and slide therethrough, as also detailed below. Openings/channels 16, 17 extend in a direction about perpendicular to the longitudinal axis 11*a*, and communicate through recesses 16*a*, 17*a* with the outer surfaces 11*c* of anchor body 11. Only recess 16*a* is shown in FIG. 1 (recess 17*a* is located on the opposite side of the recess 16*a*, i.e., on the anchor side facing away from the page). The position and size of the openings/channels 16, 17 and recesses 16*a*, 17*a* may be determined according to the characteristics of the flexible strand 30 and shuttle/pull device 40, and of the arthroscopic procedure, and the need to precisely orientate the anchor during insertion to optimize suture sliding characteristics.

Anchor 10 may be a screw-in anchor or a push-in style anchor. Anchor 10 may be formed of metal, biocompatible plastic such as PEEK or a bioabsorbable PLLA material. Socket 19 at the distal end 13 of the anchor 10 is configured to securely engage a tip of a driver, as detailed below. The socket of the anchor 10 may have any shape adapted to receive a driver tip for pushing tap-in or screw-in style anchors. Tensionable knotless anchor 10 may be made of one or more pieces, or may be provided as an integrated device.

Reference is now made to FIGS. 2-5 which illustrate the anchor 10 of FIG. 1 assembled with construct 99 (tensionable construct 99) formed of flexible strand or flexible material 30 (suture 30 or tie down suture 30) and shuttle/pull device 40 (suture passing instrument such as FiberLink™ 40 or a nitinol loop 40) attached to the flexible strand 30. In particular and exemplary-only embodiments, the flexible strand 30 is a suture strand 30 and the shuttle/pull device 40 is a suture passing device 40. Surgical construct 100 (FIG. 2) comprises tensionable knotless anchor 10 provided with flexible strand 30 passing through the body of the tensionable knotless anchor 10 and with shuttle/pull device 40 attached to the flexible strand 30. Details on assembling the construct 100 of the present invention (i.e., integrated system, surgical construct or surgical system 100 consisting of anchor 10, suture 30 and suture passing device 40 attached to the suture 30) are set forth below with reference to FIGS. 31-72.

Suture 30, which is typically braided or multi-filament, is preloaded onto the anchor by tying static knot 31, which prevents suture 30 from passing through distal blind hole 12a. The suture may also be preloaded by insert molding or by any other means known in the art. Suture 30 passes around post 20, which is large enough to allow suture 30 to take gradual turns instead of sharp turns. Suture 30 then passes through cannulation 11b and proximal blind hole 13a. Tensionable knotless anchor 10 is loaded onto a driver (not shown in FIGS. 1-5), and suture 30 is tied to the driver (for example, wrapped around a cleft of the driver) to fasten tensionable knotless anchor 10 securely to the driver.

Figure 2:
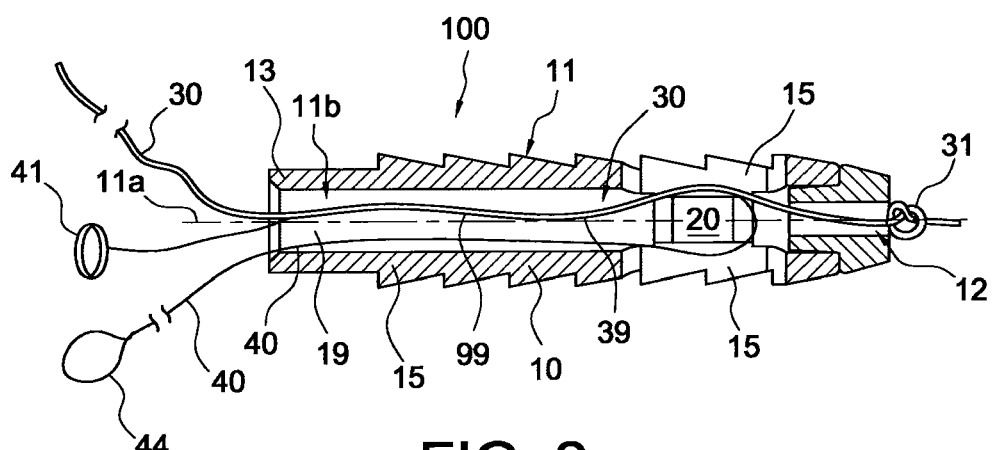
FIG. 2 is a cross-sectional view of a surgical construct according to an exemplary embodiment of the present invention (with the tensionable knotless anchor of FIG. 1, a suture and a suture passing device attached to the suture, before tensioning of the suture).

Prior to the fastening of the anchor 10 to the driver, suture passing device 40 (for example, a FiberLink™ or a nitinol loop) is threaded through suture 30 (i.e., attached to the suture 30 through splice region 39), as shown in FIG. 2. Suture passing device 40 includes an eyelet/loop 44 for passing suture and, optionally, a pull-ring 41. Suture passing device 40 passes through an aperture of suture 30, located either proximal or distal to distal blind hole 12a. It then exits an aperture of suture 30, within the tensionable knotless anchor 10, traverses around post 20, and through proximal blind hole 13a. Tensionable knotless anchor 10 loaded with tensionable construct 99 (formed of suture 30 attached to the suture passing device 40) is then secured into bone (for example, into a hole/socket/tunnel formed in the bone) by using the driver.

FIG. 3 depicts the tensionable knotless anchor 10 after it has been inserted into a drilled hole in bone, the suture released from the driver, and the driver removed. Suture 30 is then passed through (or around) the tissue 50 which is to be reattached to bone. Suture 30 is subsequently passed through eyelet/loop 44 of the suture passing device 40. Suture passing device 40 is then pulled by ring 41, thereby pulling suture 30 towards tensionable knotless anchor 10.

In FIG. 4, suture 30 has been further pulled towards tensionable knotless anchor 10 so that it doubles on itself inside tensionable knotless anchor 10. The suture passing device 40 has also been further pulled through the splice region of suture 30.

FIG. 5 illustrates surgical construct 100 with suture 30 after it has been pulled through itself, creating splice 33. Thus, the suture passing device (not visible) helps create splice 33 within tensionable knotless anchor 10 by facilitating suture 30 passing through itself. Once the suture 30 has been fully passed through itself, suture end 32 may be pulled until tissue 50 has been moved to the desired location, such as near a drilled hole in the bone. Once the desired tension and location is achieved, suture end 32 may be clipped off to complete the soft tissue repair or fixation.

The surgical construct 100 with the knotless anchor 10 and tensionable construct 99 of the invention offers the following advantages:
- the tension and/or location of the tissue may be altered after the tensionable knotless anchor is implanted;
- no knots need to be tied in the suture during the repair or fixation procedure, which makes the procedure faster, easier, and less costly;
- there is no need to load the suture outside of the tensionable knotless anchor;
- the suture may be loaded or pre-loaded on the inside of the tensionable knotless anchor; and
- no additional fasteners need to be used.

Figure 9:
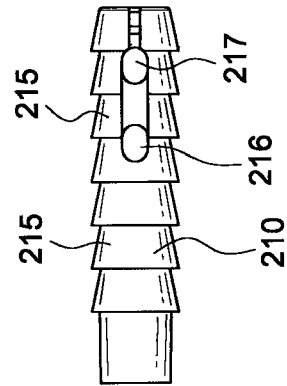
FIG. 9 is another side view of the tensionable knotless anchor of FIG. 6.
Figure 6:
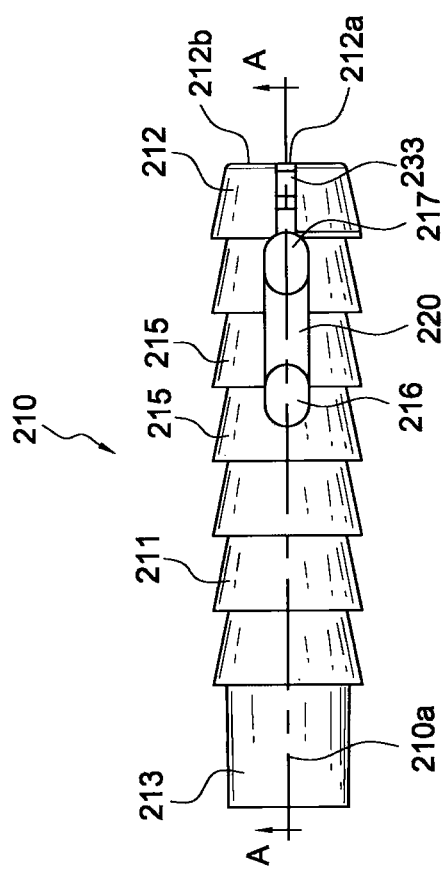
FIG. 6 illustrates a partial cross-sectional, side view of a tensionable knotless anchor according to another embodiment of the present invention.
Figure 7:
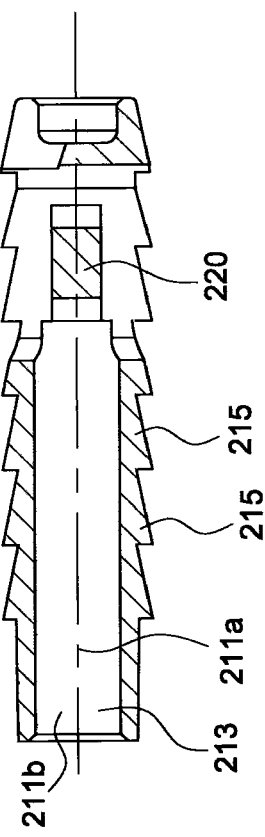
FIG. 7 illustrates a cross-sectional view of the tensionable knotless anchor of FIG. 6 (taken along line A-A').

FIGS. 6-9 illustrate various views of another tensionable knotless anchor 210 of the present invention. Tensionable knotless anchor 210 is about similar to knotless anchor 10 described above with reference to FIGS. 1-5 in that it may be used with a tensionable construct (such as construct 99 described above), but differs in that the most distal end of tensionable knotless anchor 210 is provided with a cut slot 233 that allows loading of the flexible strand 30 and suture passing device 40 onto the anchor 210. Tensionable knotless anchor 210 is provided with anchor body 211 having longitudinal axis 211a, cannulation 211b, proximal end 213 and distal end 212. Openings 216 and 217 allow threading suture(s) and/or suture passing device(s) (not shown) around post 220. Cut slot 233 is provided at most distal end of the body 210, extending from the opening 217 to a most distal end surface 212b, as shown in FIG. 6. Openings 216 and 217 are axially aligned with the cut slot 233 along longitudinal axis 211a, as shown in FIGS. 6, 7 and 9.

Although tensionable knotless anchor 210 is depicted in FIGS. 6, 7 and 9 as having ridges 215, and thus designed to be pushed into the bone, it could instead be fabricated with threads and thereby designed to be twisted or screwed into the bone.

FIGS. 10-14 illustrate surgical system 100 of FIGS. 2-5 (with knotless tensionable anchor 10, 210, suture 30 and suture passing device 40 attached to the suture 30) employed in an exemplary method of tissue repair such as a Bankart or SLAP repair, wherein the knotless suture anchor (knotless SutureTak™) simplifies arthroscopic glenohumeral joint instability repair by combining a proven and reproducible suture anchor insertion procedure with knotless soft tissue fixation.

FIG. 10 shows suture 30, preferably a UHMWPE suture, preloaded onto the anchor 10 by tying static knot 31, which prevents suture 30 from passing through distal blind hole 12a. Suture 30 is pre-attached to suture passing device 40 (for example, a FiberLink™ or a Nitinol loop 40) which is threaded through suture 30 (as shown by spliced region 39 in FIG. 10). As explained above, suture 30 is pre-loaded on anchor 10 which is loaded onto a driver (not shown in FIGS. 10-14). Suture 30 is tied to the driver (for example, wrapped around a cleft of the driver) to fasten tensionable knotless anchor 10 securely to the driver. Prior to securing knotless anchor 10 to the driver, the suture passing device 40 is attached (threaded through splice 39) to the suture 30. The construct is inserted into bone, the suture 30 untied from the driver, and the driver removed.

FIG. 10 depicts the tensionable knotless anchor 10 after it has been inserted into a drilled hole 88 in bone 80, the suture 30 released from the driver, and the driver removed. Suture 30 is passed through or around the tissue 50 which is to be reattached to bone 80. FIG. 11 depicts suture 30 passed around the tissue 50 and then threaded through eyelet/closed loop 44 of the suture passing device 40. Suture passing device 40 is pulled (as shown in FIG. 12), thereby pulling suture 30 towards tensionable knotless anchor 10.

In FIG. 13, suture 30 has been further pulled towards tensionable knotless anchor 10 so that it passed through itself inside tensionable knotless anchor 10. The suture passing device 40 has also been further pulled through suture 30. FIG. 13 illustrates surgical construct 100 with suture 30 after it has been pulled through itself, creating splice 33. The suture passing device 40 (not visible anymore in FIG. 13 as it has been completely pulled out of the suture 30) helps create splice 33 within tensionable knotless anchor 10 by facilitating suture 30 passing through itself.

Once the suture 30 has been fully passed through itself, the suture end 32 (FIG. 13) may be pulled until tissue 50 has been moved to the desired location, such as near drilled hole 88 in the bone 80. Once the desired tension and location is achieved (FIG. 14), suture end 32 may be clipped off to complete the soft tissue repair or fixation. In this manner, the suture 30 is shuttled and pulled (during the surgery) to a desired tension.

Figure 15:
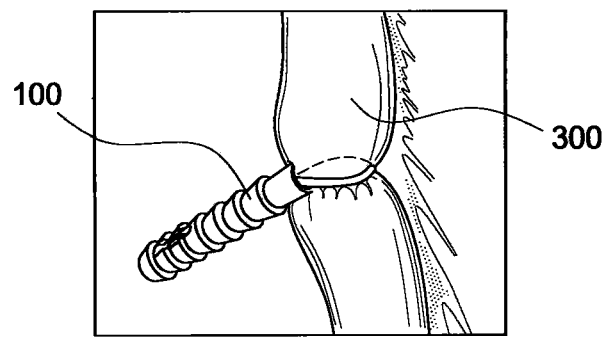
FIG. 15 illustrates the surgical construct of the present invention employed in a knotless simple stitch.

FIG. 15 illustrates surgical system 100 (with tensionable knotless anchor 10 loaded with suture passing device 40 attached to the loaded suture 30) employed in a knotless simple stitch 300.

Figure 16:
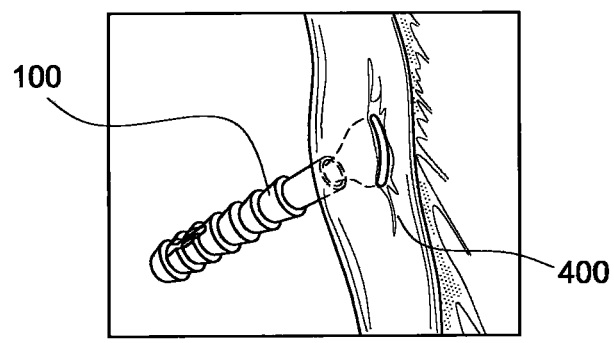
FIG. 16 illustrates the surgical construct of the present invention employed in a knotless mattress stitch.

FIG. 16 illustrates surgical system 100 (with tensionable knotless anchor 10 loaded with suture passing device 40 attached to the loaded suture 30) employed in a knotless mattress stitch 400.

FIGS. 17-29 illustrate surgical system 100 of FIGS. 2-5 (with fixation device 10, 210, flexible strand 30 and shuttling/pulling device 40 attached to the flexible strand 30) employed in another exemplary method of soft tissue repair (a Bankart and SLAP repair). A guide and drill are used to create a pilot hole precisely on the glenoid rim and the suture anchor is inserted through the same guide maintaining the same portal and drill trajectory. The knotless self-locking suture function allows the user to control the tension of the suture on the soft tissue under direct visualization.

FIGS. 17 and 18: an elevator is used to mobilize the labrum 50 on the glenoid 80. A bone socket is formed on the glenoid rim to allow subsequent insertion of surgical construct 100 of the present invention. If desired, an offset guide (FIG. 18) may be employed to aid in the placement of the anchor onto the face of the glenoid.

FIGS. 19 and 20: Surgical construct 100 is inserted into the socket in the glenoid by employing driver 90 (shown in FIG. 20). Suture 30 is released from the handle of the driver and the driver removed.

FIGS. 21-24 illustrate the passing of the suture of the surgical construct 100 around the tissue by employing suture passing and retrieving instruments known in the art (for example, a KingFisher® Suture Retriever/Tissue Grasper instrument and a SutureLasso™ instrument).

FIGS. 21 and 22: One limb of suture 30 is retrieved through the anterosuperior portal using a suture retrieval instrument 61 (for example, a KingFisher® Suture Retriever/Tissue Grasper 61). A curved SutureLasso™ instrument 62 is inserted into the anteroinferior cannula and passed through the capsulolabral tissue inferior to the anchor. Loop 63 (for example, a nitinol wire loop) is advanced into the joint. The loop is retrieved through the anterosuperior portal using the suture retrieval instrument 61.

FIGS. 23 and 24: Suture 30 is loaded through the loop 63. The wire loop 63 is retracted through the SutureLasso™ instrument 62, to pull the suture to the distal end of the SutureLasso™ instrument 62 inside the joint. The SutureLasso™ instrument 62 and the wire loop are removed together to shuttle the suture 30 through the labral tissue 50.

FIGS. 25 and 26: Suture 30 is passed through loop 44 of the suture passing device 40 (FIG. 25). The nitinol wire loop 40 is pulled away from the surgical site, to allow the suture 30 to splice itself and foam splice 33 within the body of the knotless tensionable anchor 10 of system 100 (as described above with reference to FIG. 5, for example).

FIGS. 27 and 28: The free end of suture 30 is pulled until the desired tension on the repair is achieved. A knot pusher may be used when applying tension on the repair to divert the force over the anchor and steer the tissue (labrum) 50 to the desired position. The suture is cut flush with a suture cutter instrument.

FIG. 29: Final repair 500 is shown comprising a plurality of surgical constructs 100 of the present invention.

FIG. 30 illustrates a kit 600 of the present invention including a surgical construct 100 of the present invention (for example, a 3 mm knotless SutureTak) with a spinal needle, a 1.1 mm Nitinol wire 40, a portal dilator and a SutureTak drill.

Figure 31:
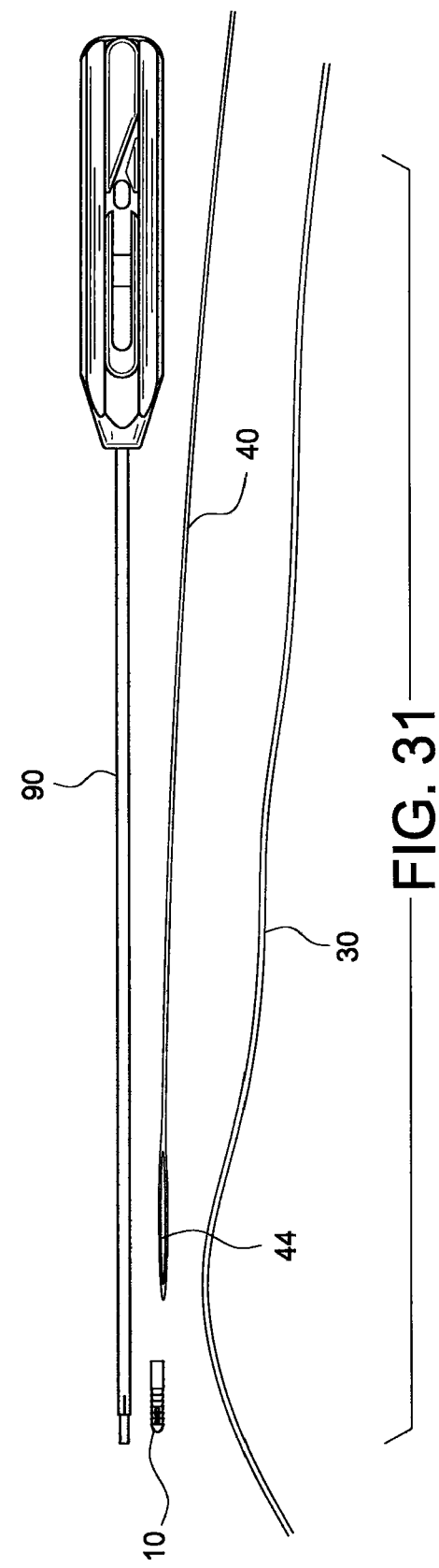

Reference is now made to FIGS. 31-72, which illustrate subsequent steps of a method of assembling a surgical construct of the present invention such as surgical construct 100 of FIG. 5 (comprising a tensionable knotless anchor (knotless SutureTak) loaded with a suture and a suture passing device attached to the suture). Assembly instructions are provided below:

FIG. 31 illustrates exemplary materials for the surgical construct 100: driver 90, suture anchor 10; nitinol wire 40 with closed loop 44; and UHMWPE braid 30. The suture component 30 is constructed from exemplary braided UHMWPE.

Figure 32:
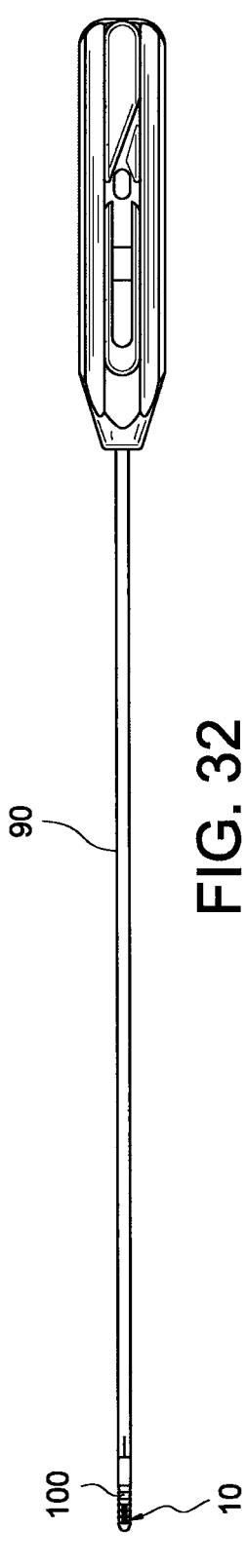

FIG. 32 illustrates driver 90 assembled with suture anchor 10 of the present invention.

FIG. 33: Tie an overhand knot 31 within few inches from one end of the braid 30. In further steps, the sides of the knot 31 will be referred to as the short end and the long end (resembling the length of suture 30 on the particular side of the knot). Preferably, there should be no tipped suture within the vicinity of the knot.

FIG. 34: Pull knot 31 tight so that the knot will fit in hole of the anchor.

FIG. 35: Optionally, place a small amount of bonding agent 31a on the knot 31.

FIG. 36: Perform the next steps with a straight needle 45 with an attached nitinol loop 40. Any alternative suture passing device may be used as long as it allows the formation of the device 100 in FIG. 43. Pierce the braid 30 with the needle 45 at a predetermined distance from the long end of the knot 31.

FIG. 37: Advance the needle 45 through the center of the braid 30, taking care not to penetrate the sheath with the tip of the needle.

FIG. 38: Allow needle 45 to exit the sheath 30 a distance from the knot 31. The needle must not be passed through glued portions of the braid 30.

FIG. 39: Pass a small length of suture 71 through the open end 44 of the nitinol wire 40.

FIG. 40: Pass both free ends of the suture 71 through the loop 45a on the needle 45 and fold the ends.

FIG. 41: Advance the needle 45 through the sheath 30 so the folded suture ends are passed through the center of the braid 30.

FIG. 42: Continue to pull the suture 71 through the braid 30 resulting in pulling the nitinol wire 40 through the center of the braid 30 as well.

Figure 43:
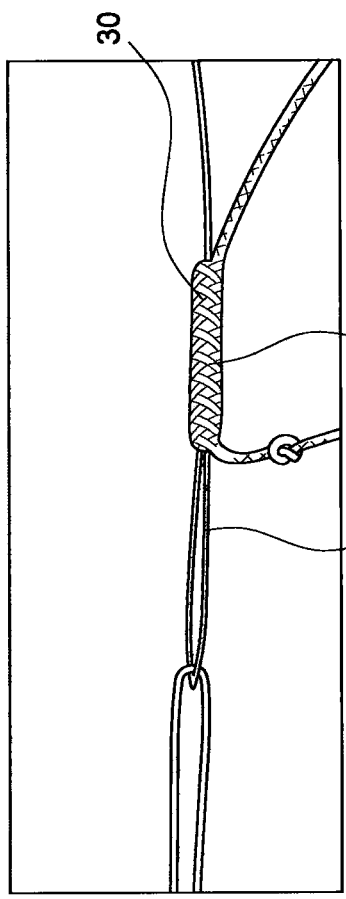

FIG. 43: Pull approximately half of the nitinol wire 40 through the braid splice 39. Ensure the shrink tube of the nitinol wire does not snag any portion of the splice 39.

Figure 44:
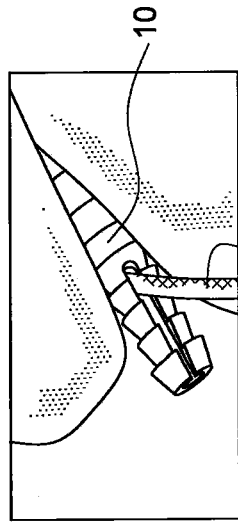

FIG. 44: Insert the long free end of the braid 30 into the side port of the anchor 10 that is on the same side as the cut slot (for example, cut slot 233).

Figure 45:
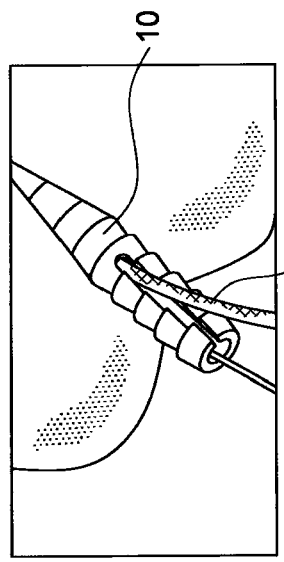

FIG. 45: Pull the braid 30 through the end hole.

Figure 46:
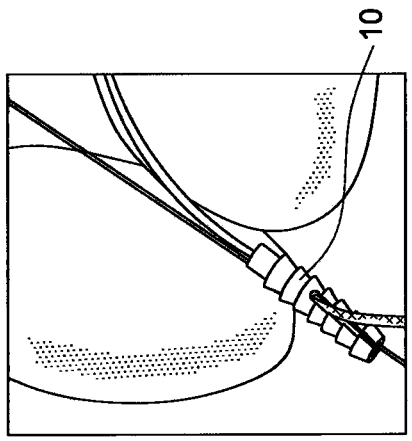

FIG. 46: Insert the non-looped end of the nitinol wire 40 through the same side port as the braid 30.

Figure 47:
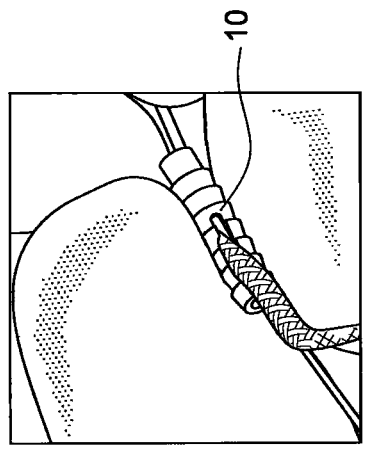

FIG. 47: Pull the nitinol 40 and the braid 30 evenly through the anchor 10 so the splice passes through the side port. Pass the splice 39 until there is sufficient access to the through hole across the side ports.

Figure 48:
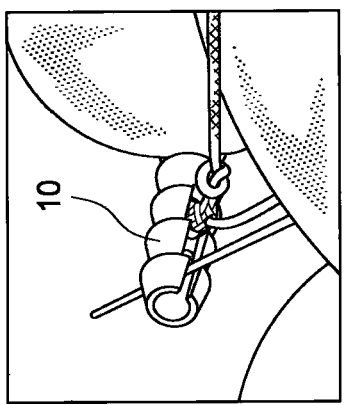

FIG. 48: Pass the looped end of the nitinol wire 40 through the side port access hole to the other side of the anchor. Pull until slack is removed.

Figure 49:
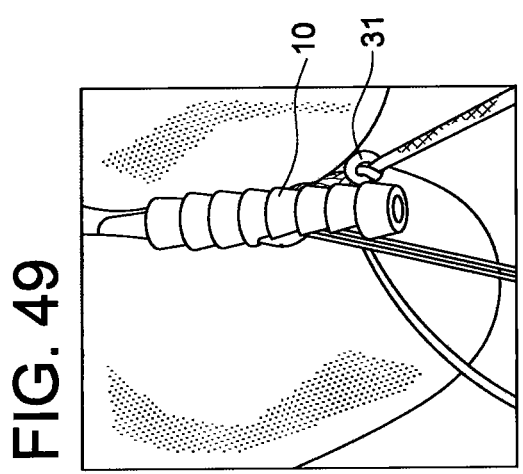

FIG. 49: Insert looped end of nitinol wire 40 back into side port and out the end hole.

Figure 50:
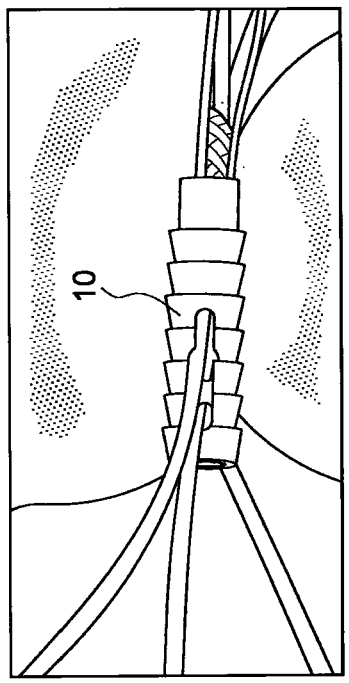

FIG. 50: Looped end of nitinol wire 40 should be on the opposite side of the post than the splice.

Figure 51:
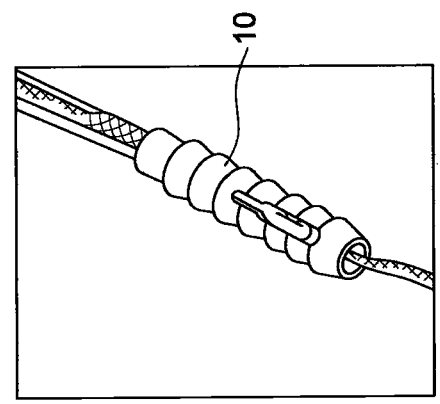

FIG. 51: Feed wire to remove all slack within and around the anchor.

Figure 52:
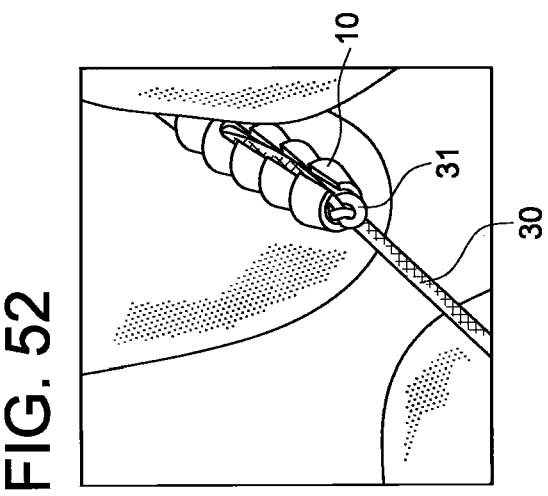

FIG. 52: Pull short end of braid 30 and knot 31 and relocate it through the cut slot 233 of the anchor.

Figure 53:
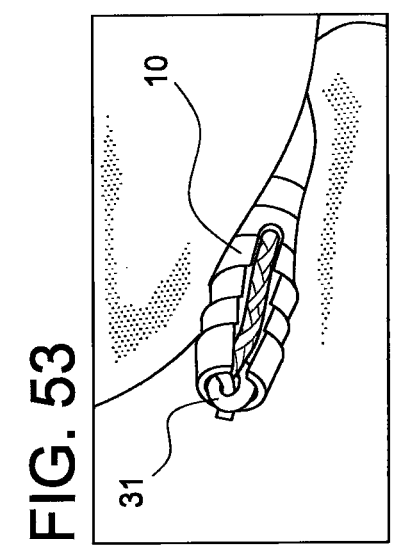

FIG. 53: Pull long end of braid 30 to seat knot 31 within the counterbore of the tip. Cut the remainder of the short end.

Figure 54:
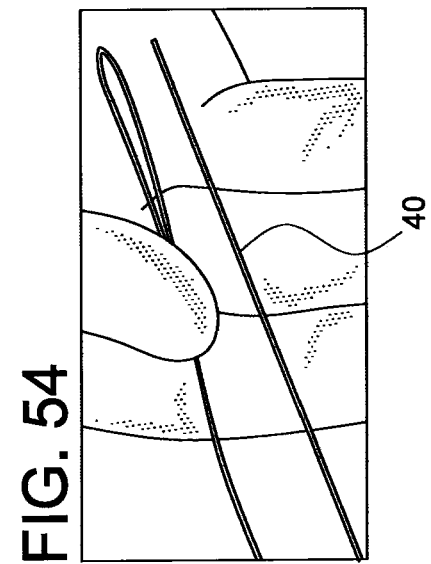

FIG. 54: Nitinol wire 40 should pull freely in both directions through the anchor 10 and braid splice 39. Adjust wire so both ends are about even.

Figure 55:
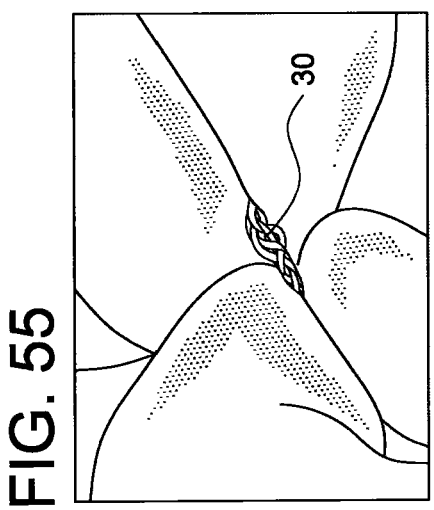

FIG. 55: From the end of the suture tail, pinch the suture 30 and compress it, to loosen the yarns within the braid.

Figure 56:
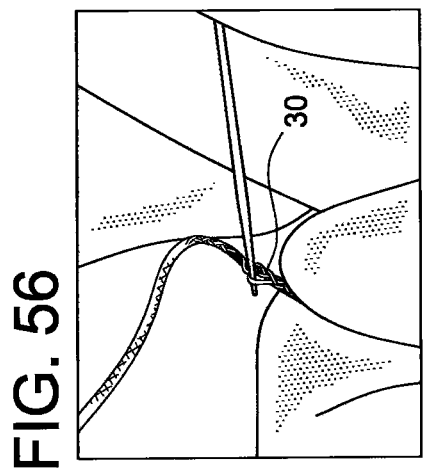

FIG. 56: With a needle, separate one of the yarns.

Figure 57:
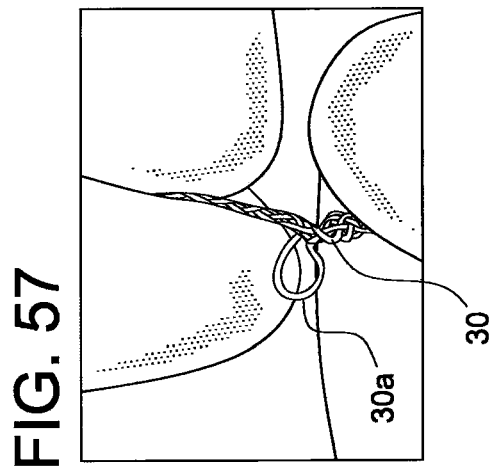

FIG. 57: Lightly pull some slack to form a small loop 30a.

FIG. 58: Carefully pull the yarn from the direction of the free suture end out from the braided suture. The braid may wrinkle as a result. Limit the amount of wrinkling in the opposite direction of the free end by limiting pulling of the yarn from that direction.

FIG. 59: Once the yarn is removed, the suture can be straightened out and smoothened, by pinching it with the finger and running it along the direction of the free end. This step is optional.

FIG. 60: Using the needle, separate out a second yarn from the site of the first yarn.

FIG. 61: Lightly pull some slack to form a small loop 30b.

FIG. 62: Carefully pull the yarn from the direction of the free suture end out from the braided suture. The braid may wrinkle as a result. Limit the amount of wrinkling in the opposite direction of the free end, by limiting pulling of the yarn from that direction.

Figure 63:
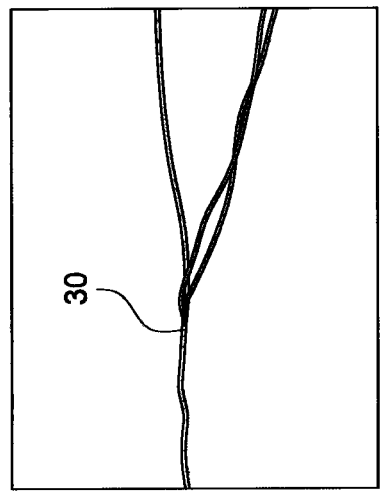

FIG. 63: Once the yarn is removed the suture can be straightened out and smoothened. The result should be similar to the picture with two loose yarns branching off from the larger.

Figure 64:
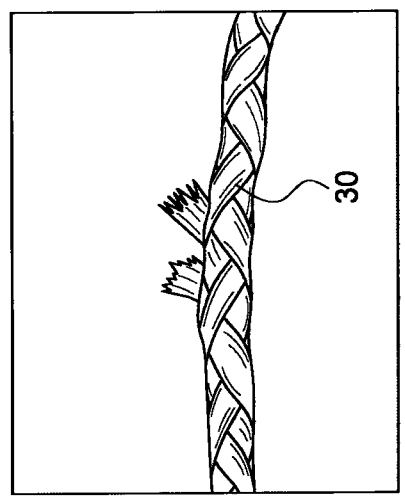

FIG. 64: The loose yarns shall be carefully trimmed close to the surface of the larger suture. The frayed edges should be pinched with the suture and brushed in the direction of the loose end, to limit how much it sticks out. Optional: step may be performed before smoothening the suture to facilitate blending the cut ends in.

Figure 65:
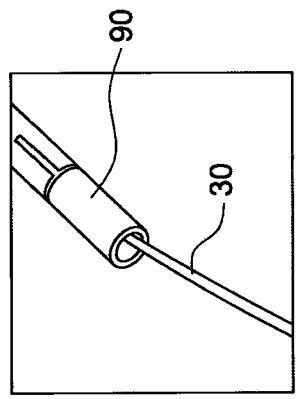

FIG. 65: Ensure there are no knots on the free end of the braid. Feed the free end of braid into the opening of the driver 90, until it can be pulled from the opposite side.

Figure 66:
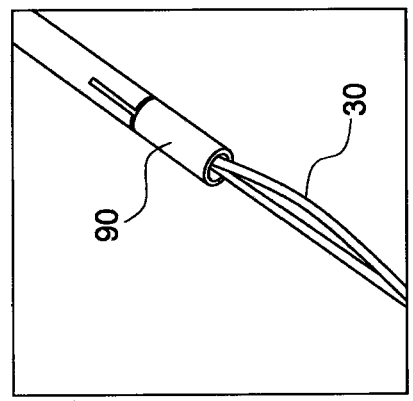

FIG. 66: Insert both ends of the nitinol wire 40 into the opening of the driver 90.

Figure 67:
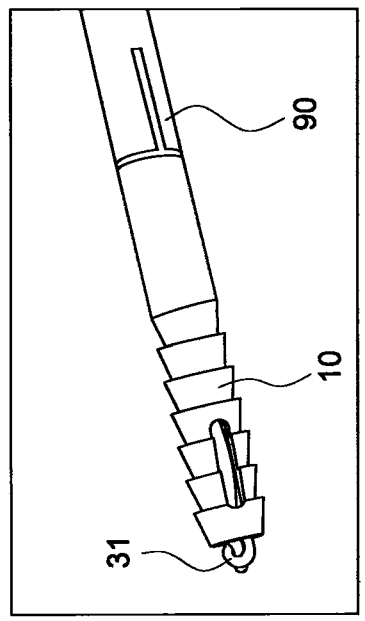

FIG. 67: Pull the slack of the braid 30 and the nitinol 40 so the anchor 10 seats in the counterbore of the driver 90.

Figure 68:
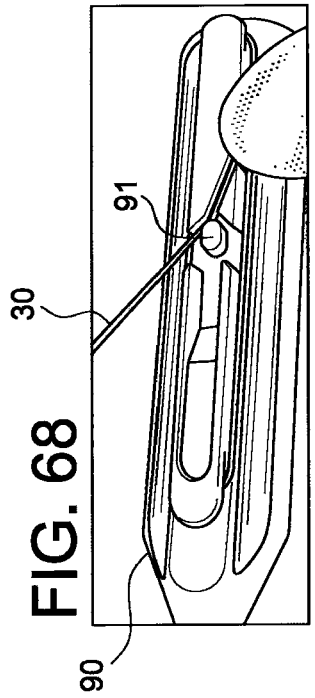

FIG. 68: Wrap the free end of the braid clockwise around keel 91 of the driver 90 once. Then pass it through the keel as shown.

Figure 69:
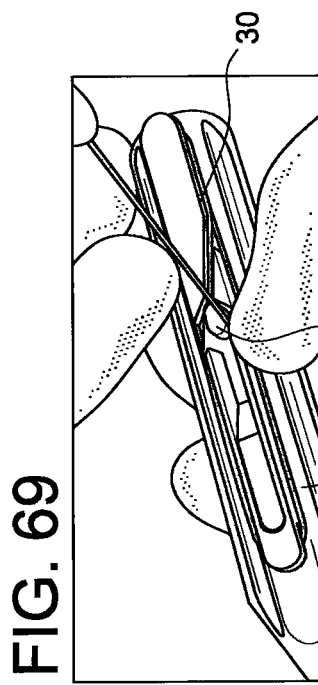

FIG. 69: Continue to pass the braid halfway around the keel counterclockwise.

Figure 70:
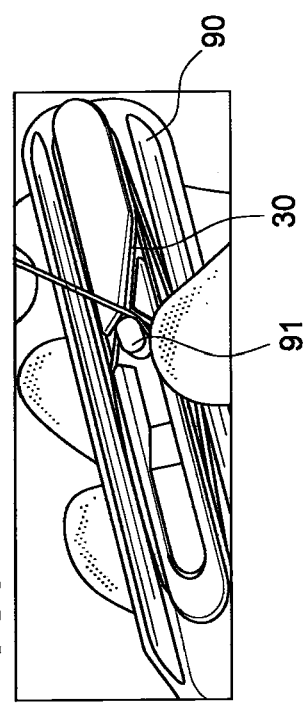

FIG. 70: Pass the braid back through the keel as shown.

Figure 71:
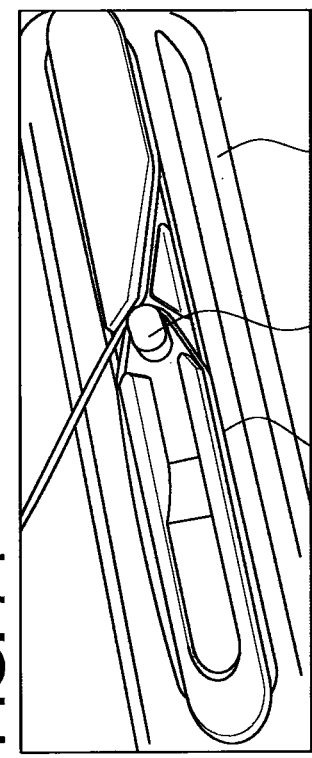

FIG. 71: Result should look as shown. A length of braid 30 should extend from keel 91. Trim excess braid (there should not be any tipped suture left on the end).

Figure 72:
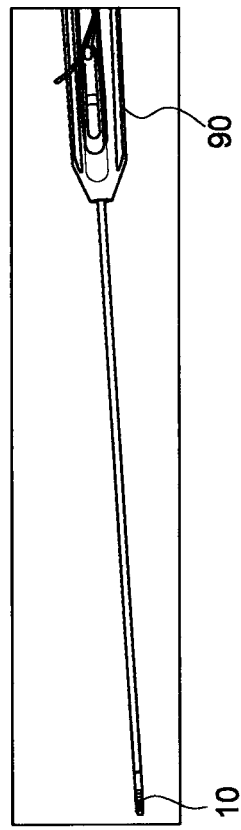

FIG. 72: Completed final assembly.

FIGS. 73-77 illustrate other exemplary embodiments of self-cinching tensionable knotless anchor 310, 310a of the present invention that allow for knotless soft tissue repairs. Tensionable knotless anchor 310, 310a has a new design that allows for a significantly smaller diameter anchor to be used (i.e., less than a 3 mm anchor). This knotless anchor uses a mechanism similar to that of the SutureTak™ which is disclosed and described in U.S. Provisional Appl. No. 61/663, 024 entitled "Tensionable Knotless Labral Anchor and Methods of Tissue Repair," filed on Jun. 22, 2012, the disclosure of which is incorporated by reference in its entirety herein.

The final splice mechanism 221 (FIG. 77) of surgical construct 200 (FIG. 77) is located outside the anchor 310a but within the drill hole 88. The suture 30 does not travel around a post to lead into the splice (as in the previously-described embodiments) but rather passes through a cannulation of the anchor body and fixed to the anchor by knot 31. The anchor 310, 310a is significantly shorter in length and diameter. The final splice construct 221 (FIG. 77) is contained in bone 80 (within bone socket or hole 88) but not within the anchor 310, 310a.

Figure 73:
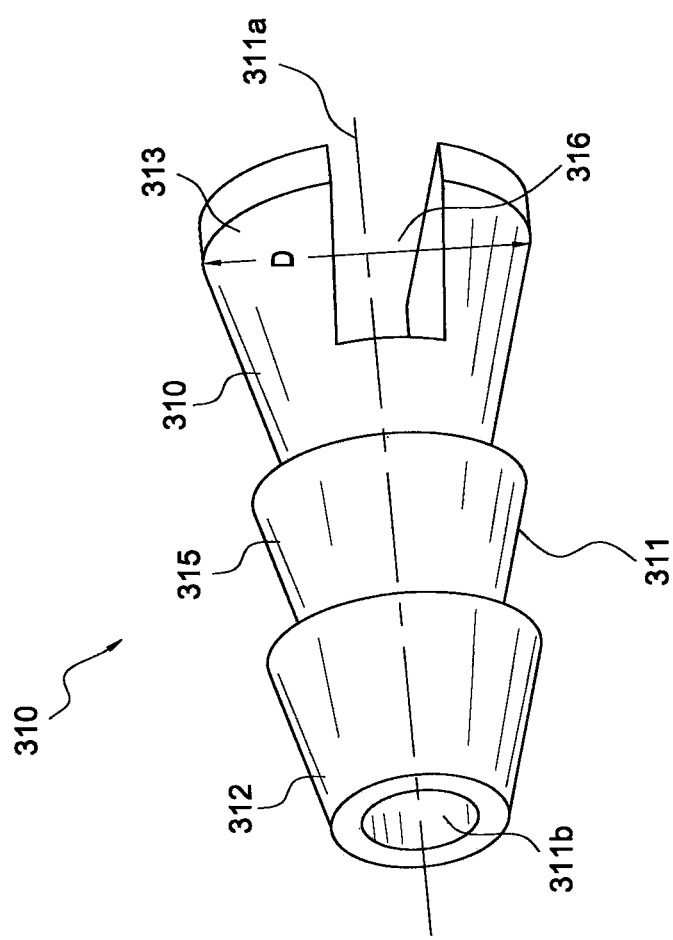
FIG. 73 illustrates a tensionable knotless anchor according to another exemplary embodiment of the present invention.

Tensionable knotless anchor 310 of FIG. 73 is about similar to knotless anchors 10, 210 described above in that it may be used with a tensionable construct (such as construct 99 described above), but differs in that anchor body 311 of anchor 310 is very small (i.e., with outer diameter D of less than 3 mm) and provided with only three exemplary ridges 315. Anchor body 311 is also provided with a longitudinal axis 311a, cannulation 311b, proximal end 313 and distal end 312. Opening 316 (located at the most proximal end) allows threading suture(s) and/or suture passing device(s) (not shown) around a post or similar structure (not shown) located within the body 311. Opening 316 extends along the longitudinal axis 311a, as shown in FIG. 73 and may have various geometries and configurations, for example, the rectangular shape shown in FIG. 73 (extending from one outer side of the anchor body to the diametrically-opposed outer side of the body).

Although tensionable knotless anchor 310 is depicted in FIG. 73 as having ridges 315, and thus designed to be pushed into the bone, it could instead be fabricated with threads and thereby designed to be twisted or screwed into the bone.

FIGS. 74-77 illustrate an exemplary method of anchoring surgical construct 200 of the present invention which includes tensionable anchor 310a assembled with construct 99 (tensionable construct 99) formed of flexible strand or flexible material 30 (suture 30 or tie down suture 30) and shuttle/pull device 40 (suture passing instrument such as FiberLink™ 40 or a nitinol loop 40) attached to the flexible strand 30. Tensionable anchor 310a of FIGS. 74-77 is similar to tensionable anchor 310 of FIG. 73 but differs in that the anchor body is not provided with rectangular opening 316 and the flexible material does not pass around a post or a similar structure.

Figure 74:
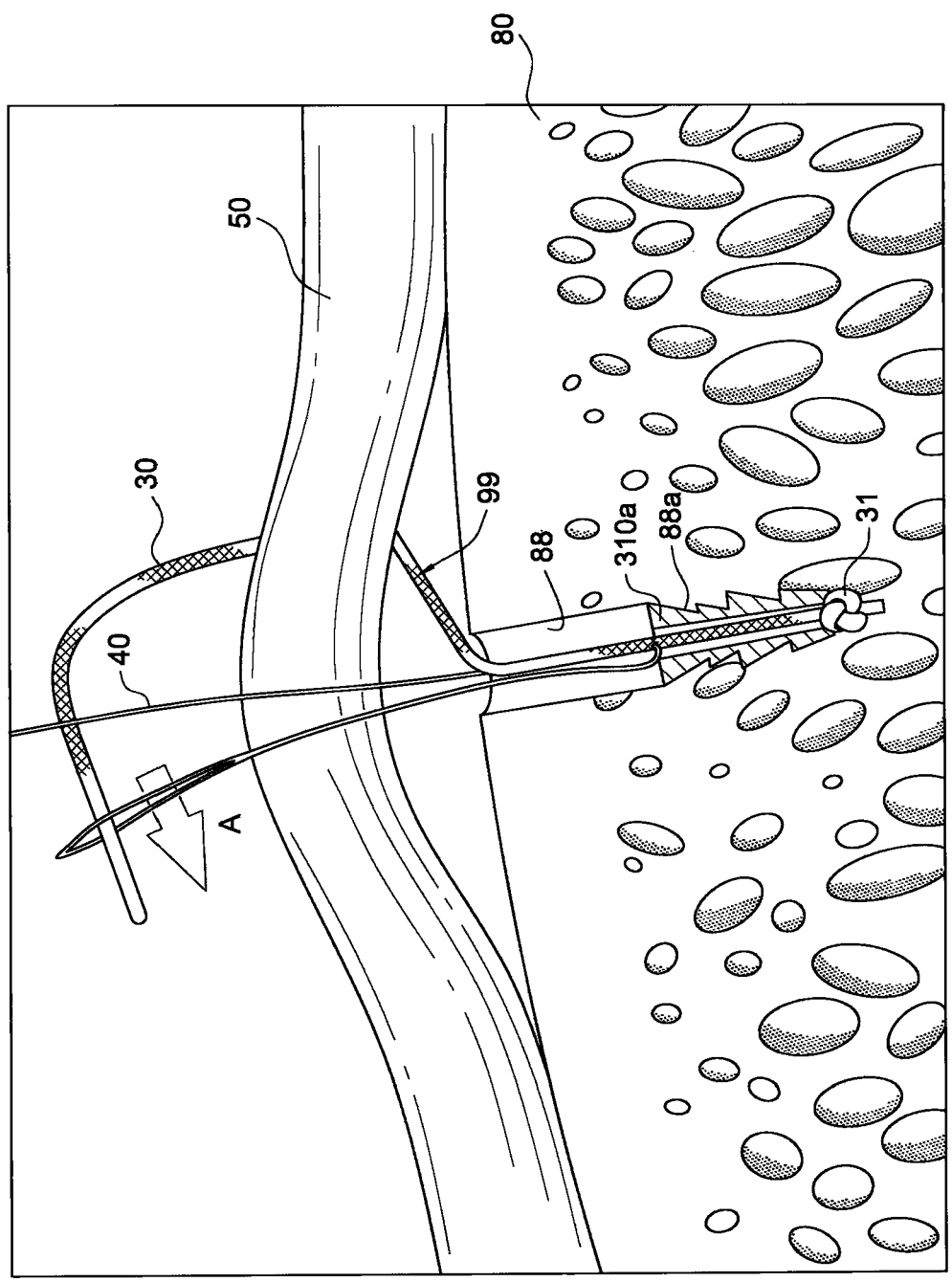
FIG. 74 is a cross-sectional view of a surgical construct according to another exemplary embodiment of the present invention (with the knotless tensionable anchor of FIG. 73 and with a suture and a suture passing device attached to the suture, before tensioning of the suture).

In this exemplary embodiment, and as shown in FIGS. 74-77, the final splice 221 is located outside the anchor body of tensionable anchor 310a but within the bone tunnel or socket 88. An exemplary method of anchoring surgical construct 200 comprises the steps of:

FIG. 74: Anchor 310a is implanted in stepped bone tunnel 88. The bone tunnel 88 may be larger than tunnel 88a where the anchor rests, to accommodate the suture splice construct. The anchor 310a is preloaded with splice making mechanism 221.

Figure 75:
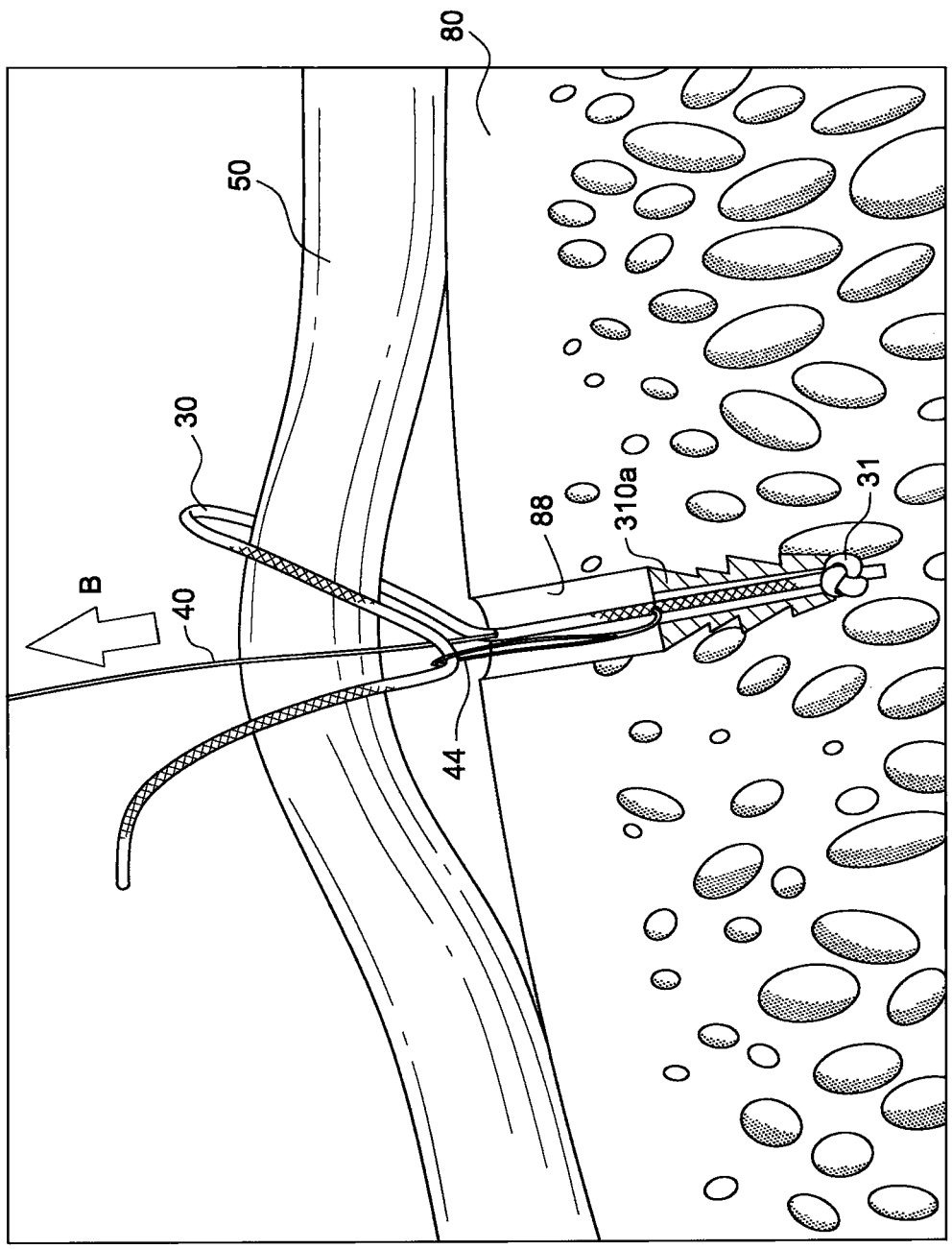
FIG. 75 illustrates the surgical construct of FIG. 74 with the suture threaded through the suture passing device.

FIG. 75: Similar to the previous design, the suture is passed around the tissue 50 and is loaded through the shuttling/pulling device 40 (Nitinol wire 40). Nitinol wire 40 is pulled to shuttle the suture 30.

Figure 76:
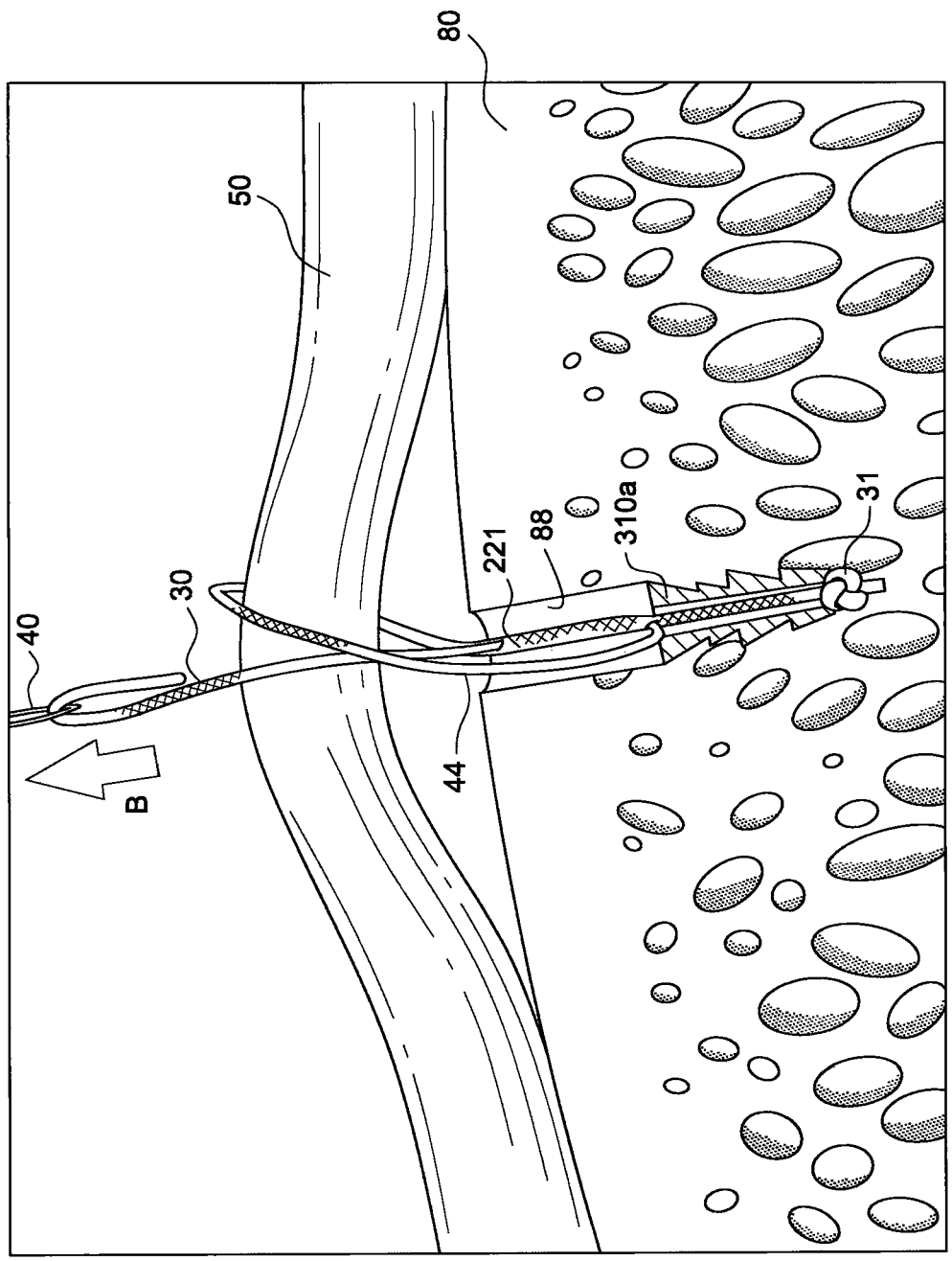
FIG. 76 illustrates the surgical construct of FIG. 75 during tensioning, wherein the suture has been pulled so that the suture passes through itself.

FIG. 76: Similar to the previous design, suture 30 is shuttled through itself to create a splice 221 with the nitinol loop 40. There is no "lead-in" from a post, but the suture can be tapered to help facilitate pulling it through.

Figure 77:
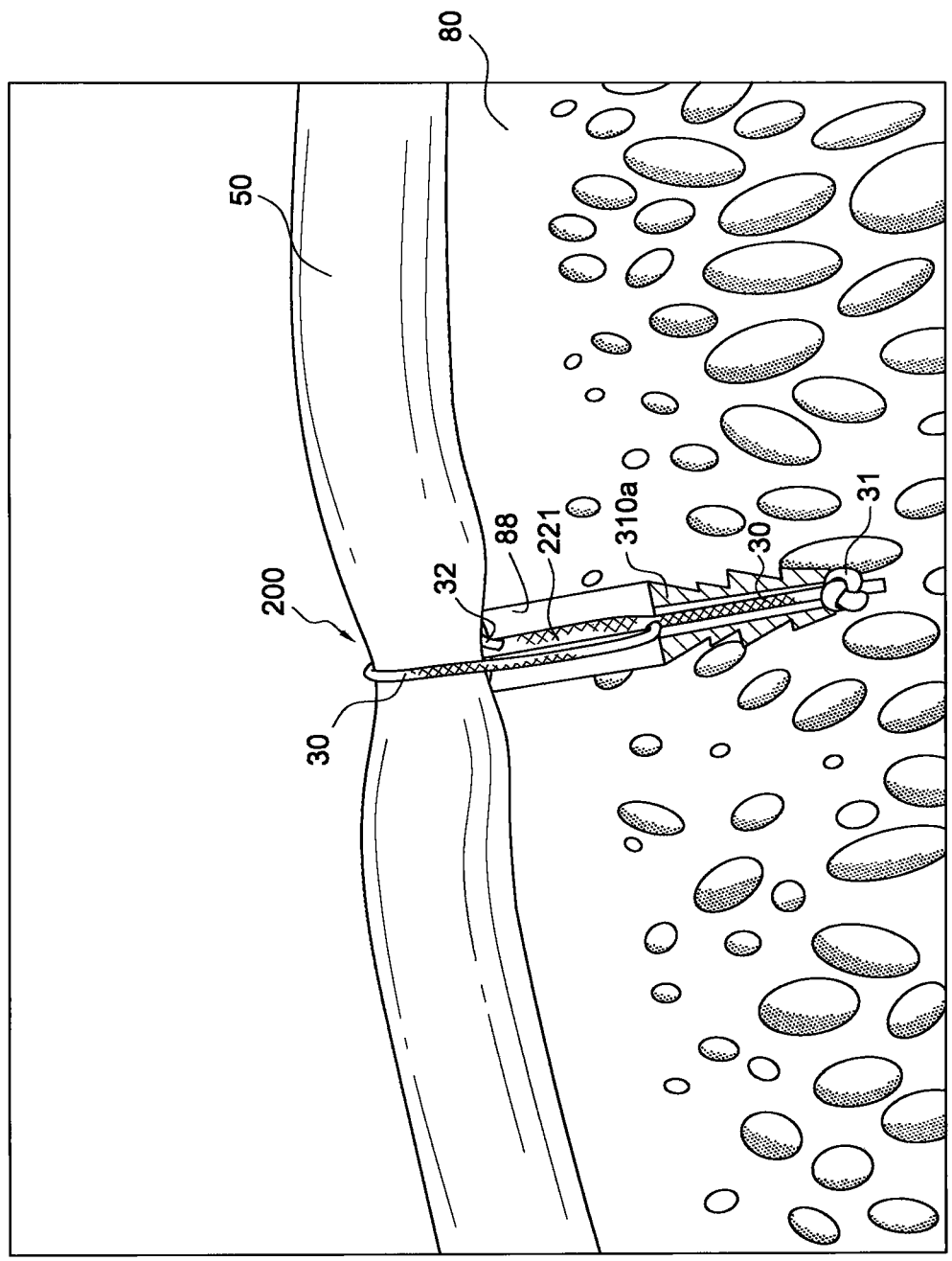
FIG. 77 illustrates the surgical construct of FIG. 76 after tensioning, wherein the suture has been pulled through itself to create a splice and the tissue has been pulled towards the bone.

FIG. 77: Same as in the previous design, the suture 30 is pulled until the tissue 50 has been moved to the desired location relative to the bone 80, and the desired tension and location have been achieved. Tension makes mechanism work and suture 30 is trimmed.

An exemplary method of tissue repair with surgical construct 200 (including tensionable anchor 310, 310a, flexible material 30 and passing device 40) comprises inter alia the steps of: (i) providing a surgical construct 99 comprising a fixation device 310a (for example, anchor) with a flexible strand 30 (for example, suture) fixed to the fixation device 310a (by knot 31, for example) and with a shuttle/pull device 40 (a suture passing instrument) attached to the flexible strand 30; (ii) inserting the fixation device 310 into bone; (iii) passing the flexible strand 30 around or through tissue to be fixated (or reattached) to bone, and then through an eyelet/loop of the shuttle/pull device 40; (iv) subsequently, pulling on the shuttle/pull device 40 to allow the flexible strand 30 to pass through itself and to form a splice 221 outside of the body of the fixation device (with the flexible strand passing through itself); and (v) pulling on the flexible strand to allow the soft tissue to achieve the desired location relative to the bone, and to allow proper tensioning of the final construct.

Figure 78:
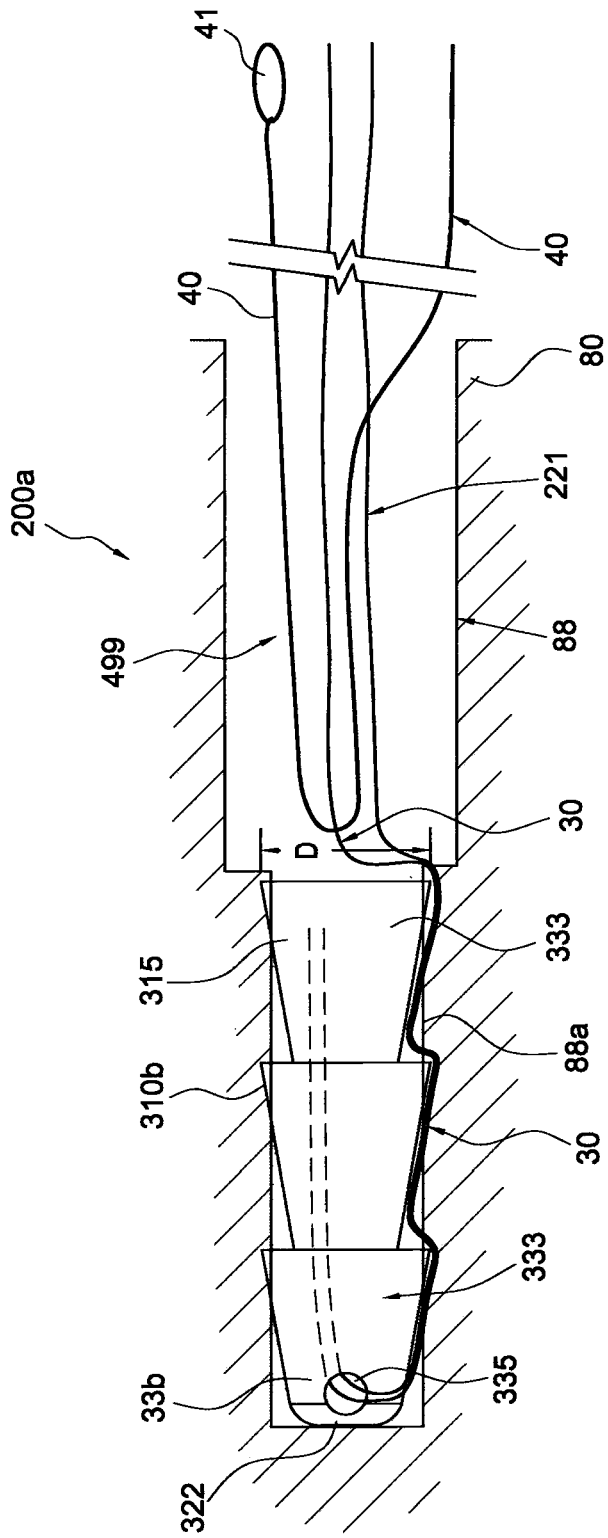
FIG. 78 illustrates a partial, cross-sectional view of a surgical construct according to another embodiment of the present invention (with a knotless tensionable anchor and a suture mechanism contained within the bone and outside of the body of the knotless tensionable anchor).

FIG. 78 illustrates another exemplary embodiment of a surgical construct 200a according to yet another embodiment of the present invention. The surgical construct 200a comprises a knotless tensionable anchor 310b and a suture mechanism 499 (similar to tensionable construct 99) that is contained within the bone and outside of the body of the knotless tensionable anchor. According to this exemplary-only embodiment, the suture end is fixed to the anchor body (which may be solid or cannulated) by overmolding the suture to the anchor body or by compressing the suture against the bone (i.e., similarly to how a PushLock® anchor (disclosed in U.S. Pat. No. 7,329,272, the disclosure of which is incorporated by reference in its entirety herewith) fixes suture into a bone tunnel or socket).

The knotless tensionable anchor 310b of FIG. 78 is similar to the designs of the anchors 310, 310a of FIGS. 73-77 in that it is also a significantly smaller diameter anchor (i.e., less than a 3 mm anchor) and uses a mechanism similar to that of the SutureTak™ which is disclosed and described in U.S. Provisional Appl. No. 61/663,024 entitled "Tensionable Knotless Labral Anchor and Methods of Tissue Repair," filed on Jun. 22, 2012, the disclosure of which is incorporated by reference in its entirety herein. However, the suture mechanism 499 (formed of flexible strand 30 and shuttle/pull device 40 attached to the flexible strand 30) is not attached to the anchor by a knot, but rather it is affixed to the body of the anchor (fixed to it) by being trapped between the anchor and bone. For this, the anchor body needs not be cannulated and could be instead a solid body (or a partially solid body).

Tensionable anchor 310b of FIG. 78 is also provided with an anchor body 333 which is very small (i.e., with an outer D of less than 3 mm) and with only three exemplary ridges 315. Anchor body 333 is also provided with a longitudinal axis 322, a proximal end 333a and distal end 333b. Opening 335 (located at the most distal end) allows threading suture(s) 30 and/or suture passing device(s) 40 to pass therethrough and aid in the fixation of the suture 40 to the anchor body 333. Opening 335 may extend about perpendicular to the longitudinal axis 332 and may have a circular configuration, as shown in FIG. 78, but may have other geometries and configurations, and may be located in other directions relative to the longitudinal axis of the anchor body. Anchor body 333 may be solid or cannulated.

Upon insertion into bone socket or tunnel 88 in bone 80, the suture mechanism forms the splice 221 similar to those formed in the above-described embodiments (i.e., with flexible strand 30 and shuttle/pull device 40 attached to the strand 30 and in a manner similar to the formation of the final constructs described above). However, splice 221 is contained within the bone 80 instead of the anchor body. As shown in FIG. 78, suture 30 is fixed to anchor body 333 either by overmolding the suture to the anchor, or by compressing the suture against the walls of bone tunnel or socket 88 in a manner similar to how a PushLock® anchor (disclosed in U.S. Pat. No. 7,329,272, the disclosure of which is incorporated by reference in its entirety herewith) fixes suture into a bone tunnel or socket.

An exemplary method of tissue repair employing anchor 310b of FIG. 78 comprises inter alia the steps of: (i) providing a fixation device 310b (for example, an anchor) with a flexible strand 30 (for example, suture) fixed to the fixation device and with a shuttle/pull device 40 (a suture passing instrument) attached to the flexible strand 30; (ii) inserting the fixation device 310b into a tunnel 88a in bone 80; (iii) passing the flexible strand 30 around or through tissue to be fixated (or reattached) to bone, and then through an eyelet/loop of the shuttle/pull device 40; (iv) subsequently, pulling on the shuttle/pull device 40 to allow the flexible strand 30 to pass through itself and to form a splice 221 outside of the body of the fixation device 310b (with the flexible strand passing through itself) but within tunnel 88 of the bone 80; and (v) pulling on the flexible strand 30 to allow the soft tissue to achieve the desired location relative to the bone, and to allow proper tensioning of the final construct.

Anchor 310, 310a, 310b may be formed of metal, biocompatible plastic such as PEEK or a bioabsorbable PLLA material. The anchors may be provided with a socket at the distal end (such as socket 19 of the anchor 10) configured to securely engage a tip of a driver. The socket of the anchor 310, 310a, 310b may have any shape adapted to receive a driver tip for pushing the anchors, for example, tap-in or screw-in style anchors. Tensionable knotless anchor 310, 310a, 310b may be made of one or more pieces, or may be provided as an integrated device.

The knotless suture constructs and systems of the present invention are used in conjunction with any knotless fixation devices which can allow a flexible strand and attached suture passing device to form a splice within the body of the fixation device. The fixation devices may be any of swivel and/or screw-in suture anchors and/or push-in suture anchors (such as an Arthrex SwiveLock® anchor, disclosed in U.S. Patent Application Publication No. 2008/0004659 or a PushLock® anchor, as disclosed in U.S. Pat. No. 7,329,272). The fixation devices may be also any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others. The fixation devices may be unitary or may be multiple-piece constructs.

The flexible strand 30 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material.

The strands may also be formed of a stiff material, or combination of stiff and flexible materials, depending on the intended application. The strands may be also coated and/or provided in different colors. The knotless anchors of the present invention can be used with any type of flexible material or suture that forms a splice and a loop.

The knotless suture constructs also include sutures that are spliced—at least in part—in a manner similar to an Arthrex ACL TightRope®, such as disclosed in U.S. Patent Application Publication Nos. 2010/0256677 and 2010/0268273, the disclosures of which are incorporated by reference herein.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. A surgical system for tissue repairs, comprising:
a fixation device comprising a cannulated body, a longitudinal axis, a proximal end and a distal end; and
a tensionable construct pre-loaded in the fixation device, the tensionable construct comprising a flexible strand and a shuttling device provided within the flexible strand, wherein both the flexible strand and the shuttling device of the tensionable construct extend through the cannulated body of the fixation device, and wherein the shuttling device is pulled out of the body of the fixation device such that the flexible strand passes through an eyelet of the shuttling device and through itself to form a knotless closed loop with an adjustable perimeter and a splice,
the splice is configured to be formed subsequent to insertion of the fixation device within bone and subsequent to attachment of soft tissue to be repaired or fixated to allow the user to control tension of the flexible strand on the soft tissue to be attached to the bone.

2. The surgical system of claim 1, wherein the tensionable construct is pre-loaded onto the fixation device by tying a static knot which prevents the flexible strand from passing through a hole at the distal end.

3. The surgical system of claim 1, wherein the tensionable construct consists of the flexible strand and the shuttling device attached to the flexible strand.

4. The surgical system of claim 1, wherein the fixation device is an anchor with a post and a pair of openings symmetrically positioned relative to the post, the pair of openings extending in a direction about transversal to the longitudinal axis of the body such that the tensionable construct passes through the body of the fixation device and around the post.

5. The surgical system of claim 1, wherein the flexible strand is a suture formed of ultrahigh molecular weight polyethylene.

6. The surgical system of claim 1, wherein the shuttling device is a suture passing instrument.

7. The surgical system of claim 1, wherein the shuttling device is a nitinol loop.

8. The surgical system of claim 1, wherein the body has an opening at a most proximal end for receiving a driver head for driving the fixation device, and an opening at a most distal end for receiving and housing a knot of the flexible strand.

9. The surgical system of claim 1, wherein the fixation device is an anchor with an anchor body provided with a plurality of circumferential ribs extending from an outer surface of the anchor body.

10. The surgical system of claim 1, wherein the splice is formed within the body of the fixation device.

11. The surgical system of claim 1, wherein the splice is formed outside the body of the fixation device.

12. The surgical system of claim 1, wherein the body has an outer diameter less than about 3 mm.

13. The surgical system of claim 1, wherein the tissue is soft tissue.

14. A surgical construct for tissue repairs, comprising:
a fixation device comprising a cannulated body, a longitudinal axis, a proximal end and a distal end, the body having an outer diameter of less than about 3 mm and comprising a plurality of ridges; and
a tensionable construct pre-loaded on the fixation device, the tensionable construct consisting of a flexible strand and a shuttling device provided within the flexible strand, wherein both the flexible strand and the shuttling device of the tensionable construct extend through the cannulated body of the fixation device, and wherein the shuttling device is pulled out of the body of the fixation device such that the flexible strand passes through an eyelet of the shuttling device and through itself to form a knotless closed loop with an adjustable perimeter and a splice,
the splice is configured to be formed subsequent to insertion of the fixation device within bone and subsequent to attachment of soft tissue to be repaired or fixated to allow the user to control tension of the flexible strand on the soft tissue to be attached to the bone.

15. The surgical construct of claim 14, wherein the flexible strand is affixed to the body of the fixation device by passing the flexible strand through an opening at a distal end of the body and tying a static knot which prevents the flexible strand from passing through the opening at the distal end.

16. The surgical construct of claim 14, wherein the splice is formed outside the body of the fixation device.

17. The surgical construct of claim 14, wherein the shuttling device is a suture passing instrument or a wire loop.

* * * * *